United States Patent
Ibuki et al.

(10) Patent No.: US 11,746,331 B2
(45) Date of Patent: Sep. 5, 2023

(54) ENDODERMAL CELL POPULATION, AND METHOD FOR PRODUCING CELL POPULATION OF ANY OF THREE GERM LAYERS FROM PLURIPOTENT CELL

(71) Applicants: KANEKA CORPORATION, Osaka (JP); NATIONAL CENTER FOR GLOBAL HEALTH AND MEDICINE, Tokyo (JP)

(72) Inventors: Masato Ibuki, Kobe (JP); Hitoshi Okochi, Tokyo (JP); Shigeharu Yabe, Tokyo (JP)

(73) Assignees: KANEKA CORPORATION; NATIONAL CENTER FOR GLOBAL HEALTH AND MEDICINE, Tokyo (JP)

( * ) Notice: Subject to any disclaimer, the term of this patent is extended or adjusted under 35 U.S.C. 154(b) by 424 days.

(21) Appl. No.: 16/481,418

(22) PCT Filed: Jan. 26, 2018

(86) PCT No.: PCT/JP2018/002545
§ 371 (c)(1),
(2) Date: Jul. 26, 2019

(87) PCT Pub. No.: WO2018/139600
PCT Pub. Date: Aug. 2, 2018

(65) Prior Publication Data
US 2022/0017869 A1    Jan. 20, 2022

(30) Foreign Application Priority Data

Jan. 27, 2017 (JP) ................................. 2017-012802

(51) Int. Cl.
*C12N 5/071* (2010.01)
(52) U.S. Cl.
CPC ......... *C12N 5/0678* (2013.01); *C12N 5/0676* (2013.01); *C12N 2500/24* (2013.01); *C12N 2500/44* (2013.01); *C12N 2501/15* (2013.01); *C12N 2501/33* (2013.01); *C12N 2506/45* (2013.01)

(58) Field of Classification Search
CPC ................................................. C12N 5/0678
See application file for complete search history.

(56) References Cited

U.S. PATENT DOCUMENTS

| | | |
|---|---|---|
| 2009/0298169 A1 | 12/2009 | Dalton et al. |
| 2013/0022986 A1 | 1/2013 | Hosoya et al. |
| 2013/0137130 A1 | 5/2013 | Wells et al. |
| 2013/0210060 A1 | 8/2013 | Hosoya et al. |
| 2013/0309768 A1 | 11/2013 | Furue et al. |
| 2015/0329821 A1 | 11/2015 | Ang et al. |
| 2015/0368616 A1 | 12/2015 | Jensen et al. |
| 2016/0053230 A1 | 2/2016 | Tomizawa |
| 2016/0237401 A1 | 8/2016 | Vallier et al. |
| 2017/0304369 A1 | 10/2017 | Ang et al. |
| 2022/0017869 A1 | 1/2022 | Ibuki et al. |

FOREIGN PATENT DOCUMENTS

| | | | |
|---|---|---|---|
| CN | 101541953 A | 9/2009 | |
| CN | 108138102 A | 6/2018 | |
| CN | 111542598 A | 8/2020 | |
| CN | 112912490 A | 6/2021 | |
| CN | 115135755 A | 9/2022 | |
| JP | 2008-525040 A | 7/2008 | |
| JP | 2009-513143 A | 4/2009 | |
| JP | 2010-528295 A | 8/2010 | |
| JP | 2012-507281 A | 3/2012 | |
| JP | 2012-527880 A | 11/2012 | |
| JP | 2012-533323 A | 12/2012 | |
| JP | 2013-536685 A | 9/2013 | |
| JP | 2013536685 | * 9/2013 | ........... C12N 5/0768 |
| JP | 2014-501518 A | 1/2014 | |
| JP | 2014-504856 A | 2/2014 | |
| JP | 2015-192681 A | 11/2015 | |
| JP | 2016-26490 A | 2/2016 | |
| JP | 2016-73323 A | 2/2016 | |
| JP | 2016-506736 A | 3/2016 | |
| JP | 2016-514481 A | 5/2016 | |
| JP | 2017-534269 A | 11/2017 | |
| WO | WO 2006/071911 A2 | 7/2006 | |
| WO | WO 2006/126574 A1 | 11/2006 | |

(Continued)

OTHER PUBLICATIONS

D'Amour et al, 2006 (cited on IDS filed on Oct. 24, 2019) (Year: 2006).*
Machine Translation of WO 2012/020845 A1 (Year: 2012).*
Machine Translation of JP2013536685 (Year: 2013).*
Brewer et al. (1993, J. Neuroscience Res., vol. 35, pp. 567-576). (Year: 1993).*
Vallier et al. (2009, PLoS One, vol. 4(6), pp. 1-13) (Year: 2009).*
D'Amour et al., "Production of pancreatic hormone-expressing endocrine cells from human embryonic stem cells," Nature Biotechnology, vol. 24, No. 11, 2006 (published online Oct. 19, 2006), pp. 1-11.

(Continued)

*Primary Examiner* — Anoop K Singh
*Assistant Examiner* — David A Montanari
(74) *Attorney, Agent, or Firm* — Birch, Stewart, Kolasch & Birch, LLP

(57) ABSTRACT

An object of the present invention is to provide an endodermal cell population for obtaining optimal somatic cells as cell therapy preparations. The endodermal cell population of the present invention has a reduced content proportion of undifferentiated cells in the cell population and contains endodermal cells differentiable into optimal somatic cells as cell therapy preparations. Further, a somatic cell derived from the endodermal cell population of the present invention has excellent therapeutic effects as a cell therapy preparation.

11 Claims, 12 Drawing Sheets
Specification includes a Sequence Listing.

(56) References Cited

FOREIGN PATENT DOCUMENTS

| WO | WO 2007/051038 | A2 | | 5/2007 | | |
|---|---|---|---|---|---|---|
| WO | WO 2008/147982 | A1 | | 12/2008 | | |
| WO | WO 2010/053472 | A1 | | 5/2010 | | |
| WO | WO 2010/136583 | A2 | | 12/2010 | | |
| WO | WO 2011/011349 | A2 | | 1/2011 | | |
| WO | WO 2011/081222 | A1 | | 7/2011 | | |
| WO | WO 2012/020845 | A1 | | 2/2012 | | |
| WO | WO-2012020845 | A1 | * | 2/2012 | ............ | A61K 35/39 |
| WO | WO 2012/030538 | A2 | | 3/2012 | | |
| WO | WO 2012/078153 | A1 | | 6/2012 | | |
| WO | WO 2012/081029 | A1 | | 6/2012 | | |
| WO | WO 2014/124172 | A1 | | 8/2014 | | |
| WO | WO 2014/165663 | A1 | | 10/2014 | | |
| WO | WO 2016/016894 | A1 | | 2/2016 | | |
| WO | WO 2021/180984 | A1 | | 9/2021 | | |
| WO | WO 2022/213731 | A1 | | 10/2022 | | |

OTHER PUBLICATIONS

International Search Report for International Application No. PCT/JP2018/002545, dated Apr. 25, 2018, with English translation.
Shiraki et al., "Methionine Metabolism Regulates Maintenance and Differentiation of Human Pluripotent Stem Cells," Cell Metabolism, vol. 19, No. 5, May 6, 2014, pp. 780-794.
Matsuno et al., "Redefining definitive endoderm subtypes by robust induction of human induced pluripotent stem cells," Differentiation (2016) vol. 92, pp. 281-290.
Office Action dated Jan. 4, 2022, in Japanese Patent Application No. 2018-564659.
Communication Pursuant to Rule 164(1) EPC dated Aug. 14, 2020, in European Patent Application No. 18744653.9.
Pagliuca et al., "Generation of Functional Human Pancratic β Cells In Vitro," Cell (Oct. 9, 2014), vol. 159, pp. 428-439.
Schulz et al., "A Scalable System for Production of Functional Pancreatic Progenitors from Human Embryonic Stem Cells," PLoS One (May 2012), vol. 7, Issue 5, e37004, pp. 1-17.
Japanese Notice of Reasons for Rejection for Japanese Application No. 2018-564659, dated Aug. 31, 2021, with an English translation.
Extended European Search Report dated Mar. 2, 2023, in European Patent Application No. 22207728.1.
Chinese Office Action and Search Report for Chinese Application No. 201880008797.6, dated Nov. 14, 2022, with an English translation.
Cui et al., "Improved passage induction method efficiently induces human embryonic stem cells to differentiate into endoderm cells," Journal of Reproductive Medicine, vol. 30, No. 2, 2021, pp. 230-235, with an English abstract.
Sun et al., "Activin A's promotion of definitive endoderm differentiation from human embryonic stem cells," Journal of Northwest A&F University (Nat. Sci. Ed.), vol. 40, No. 6, 2012, pp. 13-18, with an English abstract.
Xu et al., "Activin, BMP and FGF pathways cooperate to promote endoderm and pancreatic lineage cell differentiation from human embryonic stem cells," Mechanisms of Development, vol. 128, 2011, pp. 412-427.

* cited by examiner

[Fig. 1]
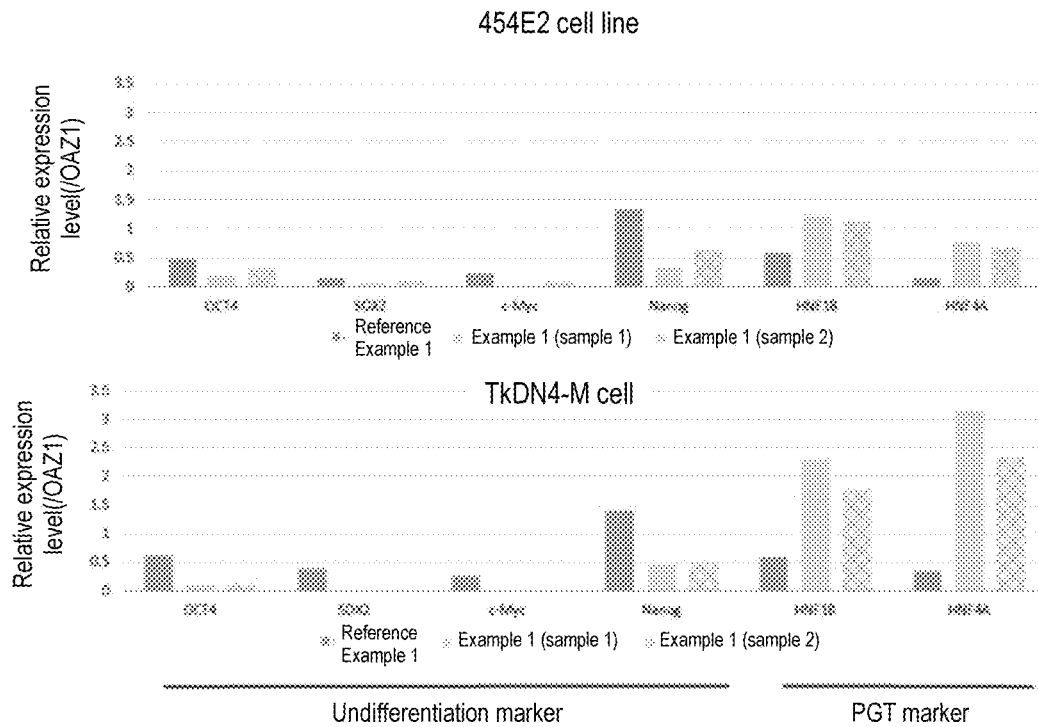
[Fig. 2]
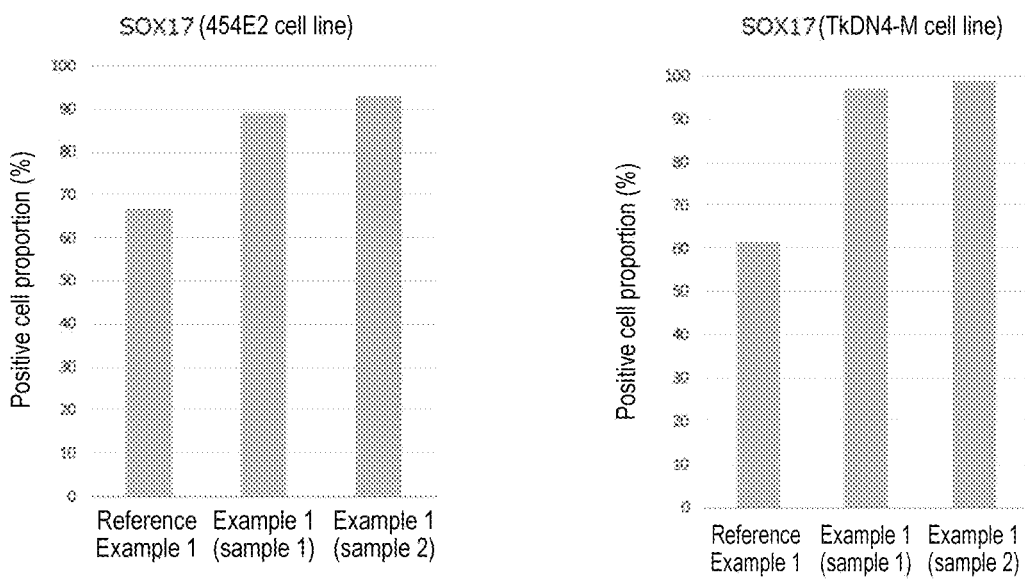

[Fig. 3]
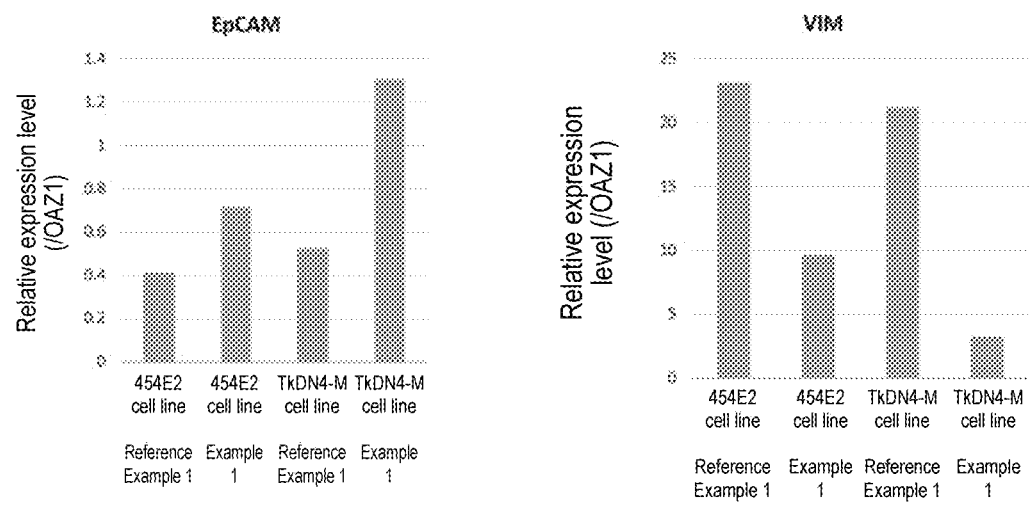
[Fig. 4]
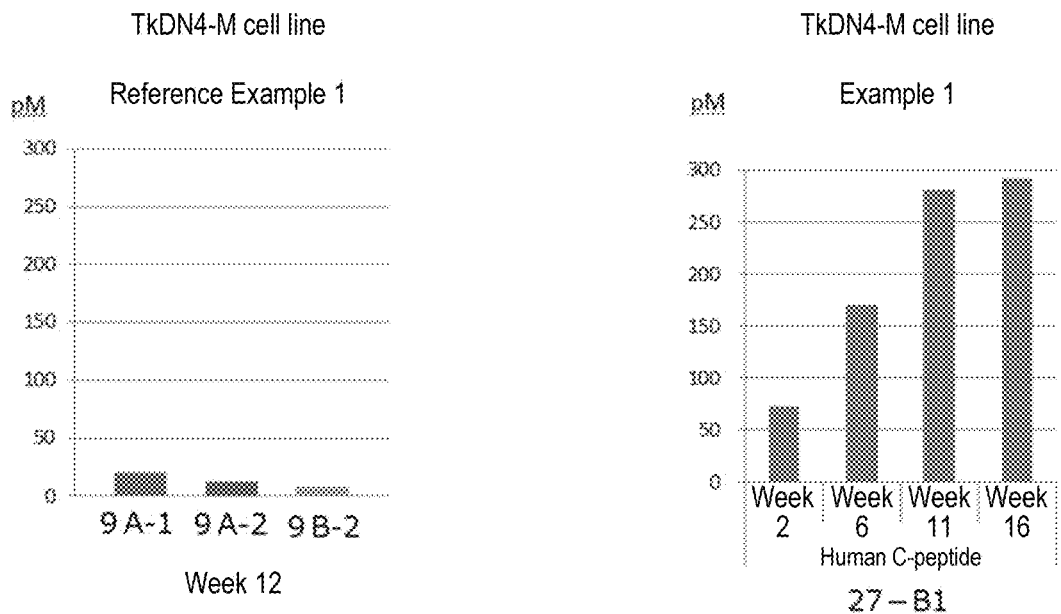

[Fig. 5]
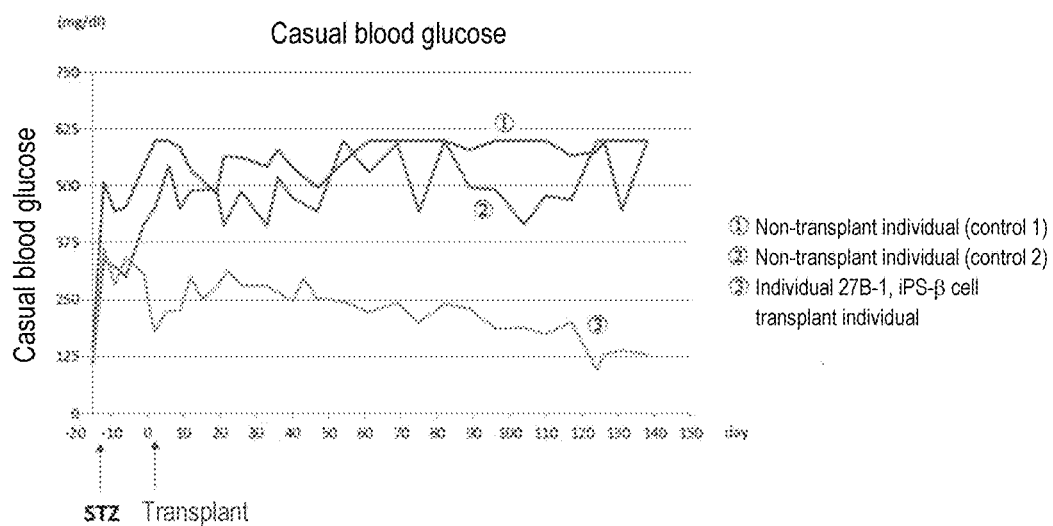
[Fig. 6]
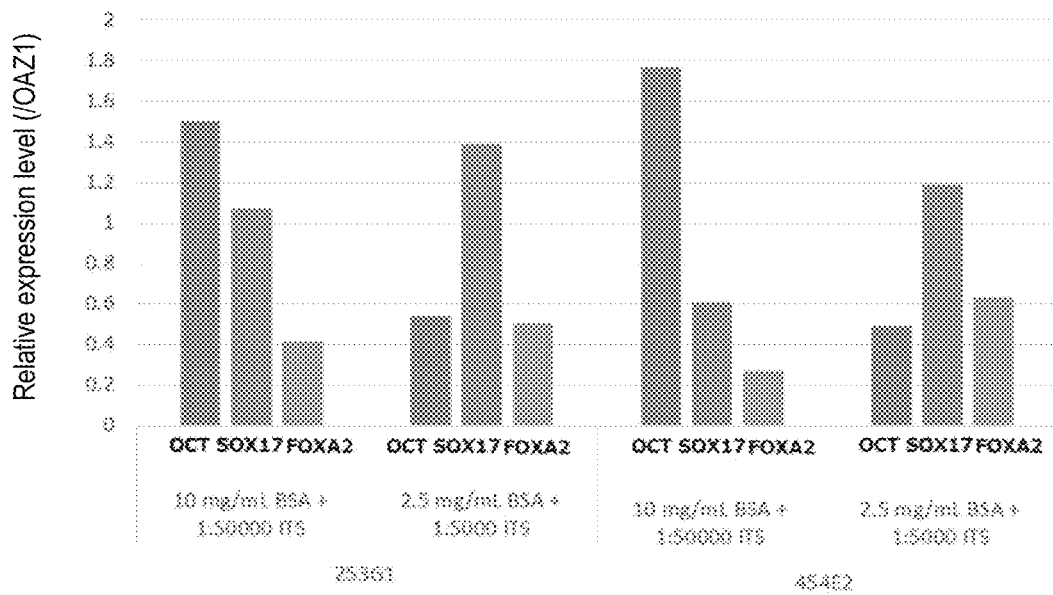

[Fig. 7]
TkDN4-M cell line
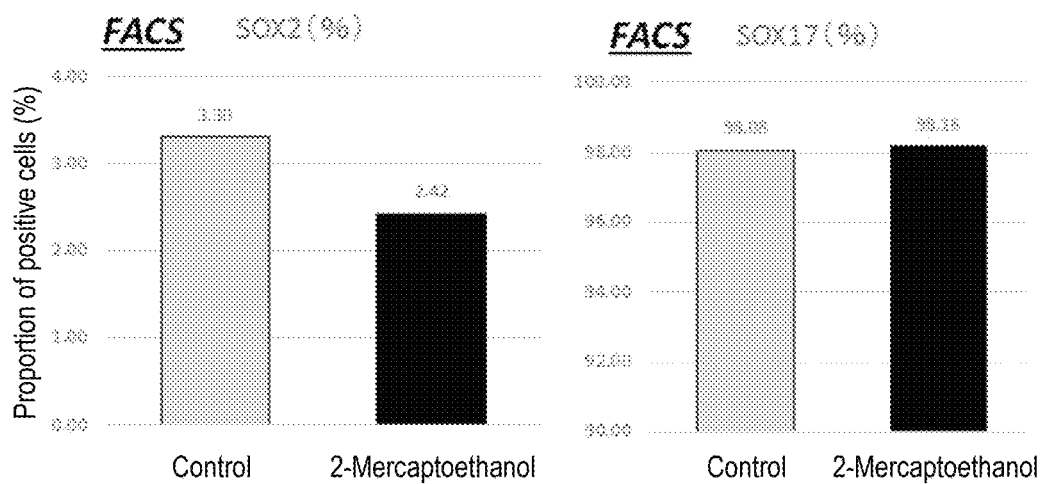
[Fig. 8]
TkDN4-M cell line
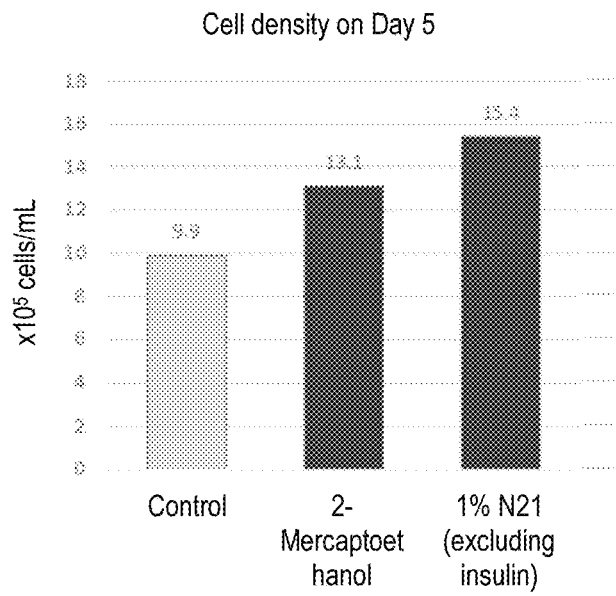

[Fig. 9]
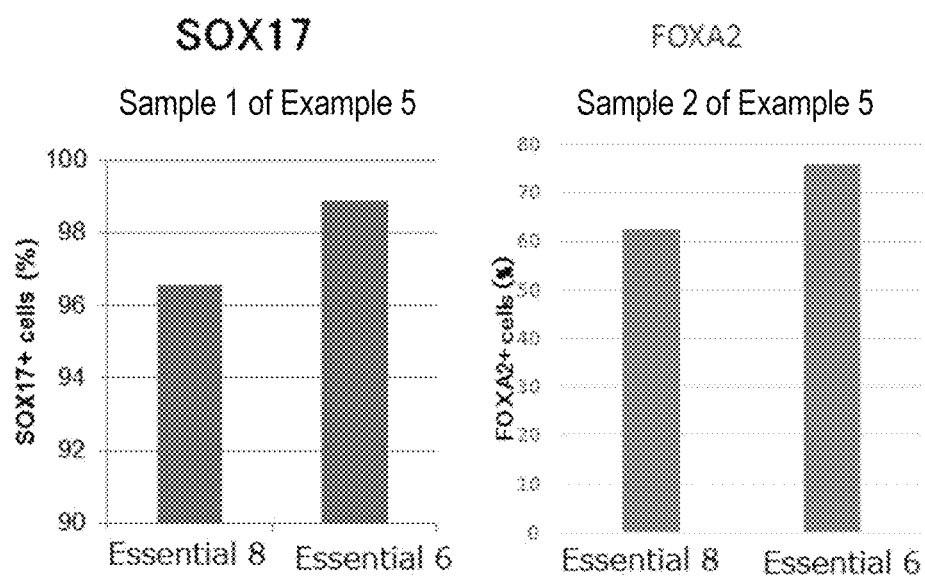

[Fig. 10]
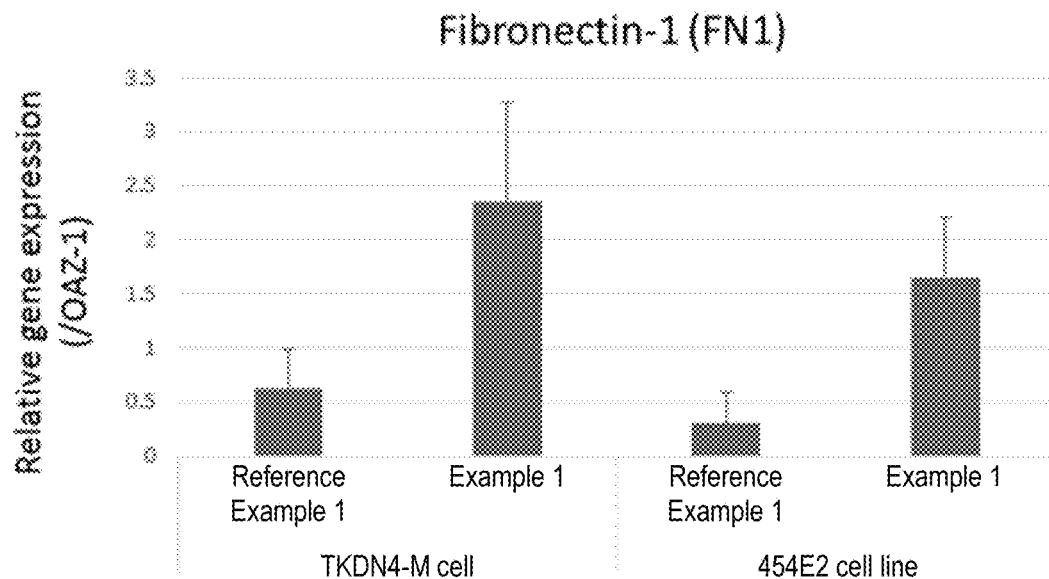
[Fig. 11]
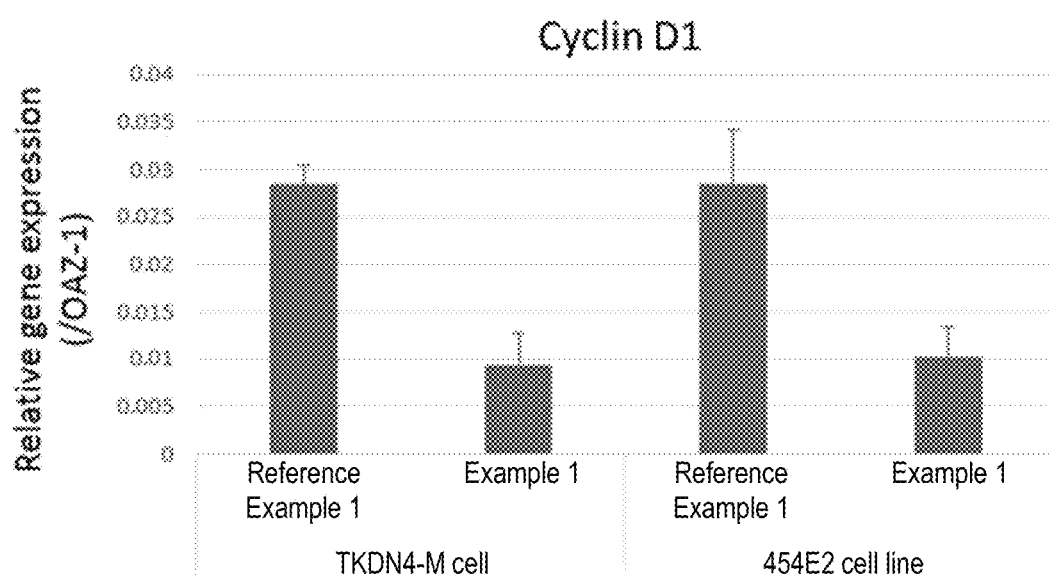

[Fig. 12]
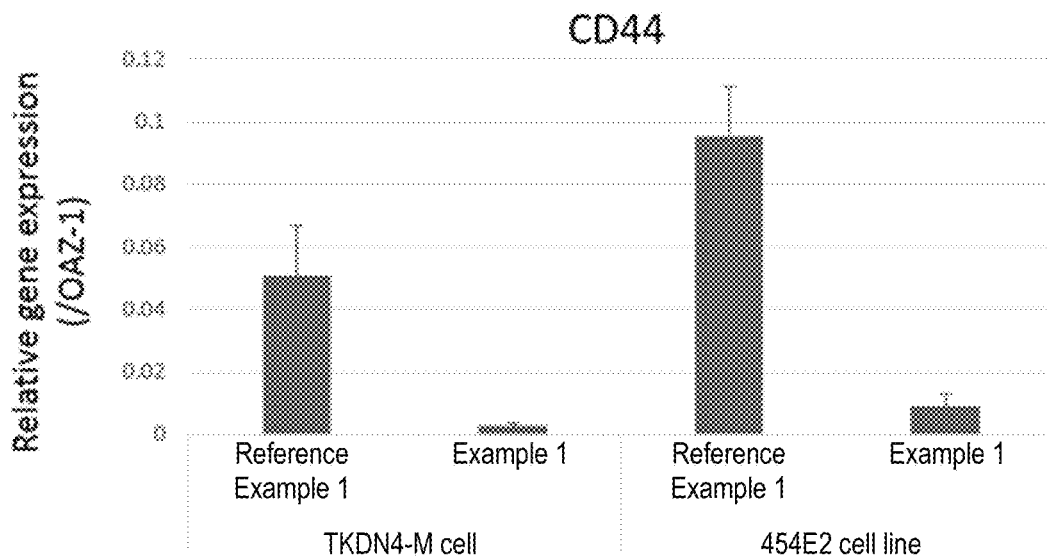
[Fig. 13]
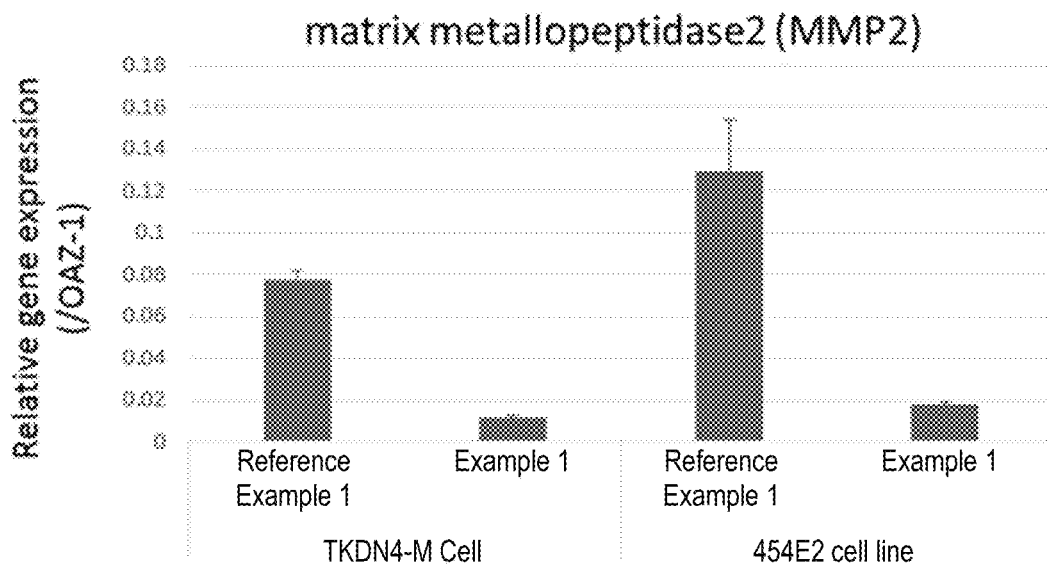

[Fig. 14]
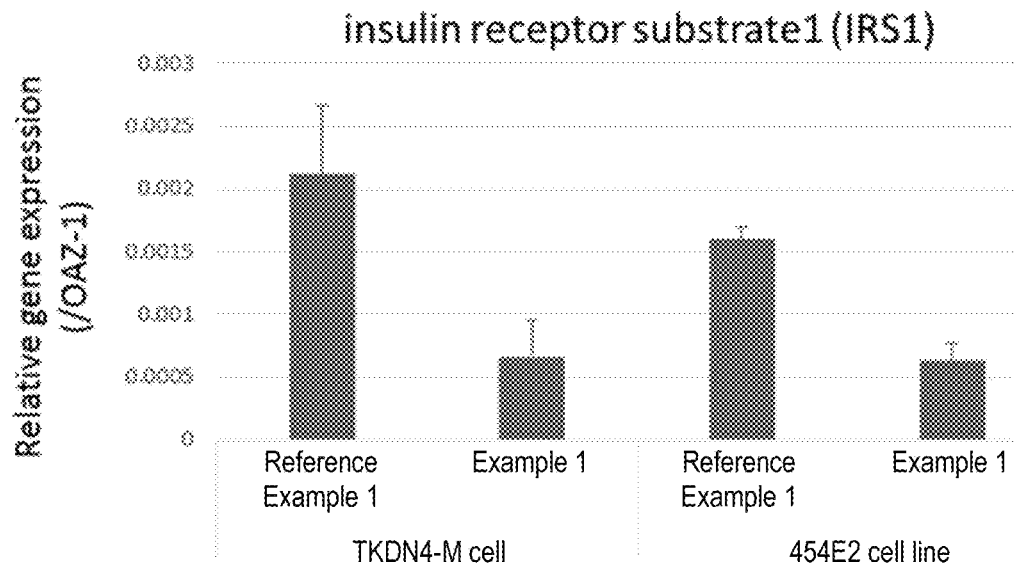
[Fig. 15]
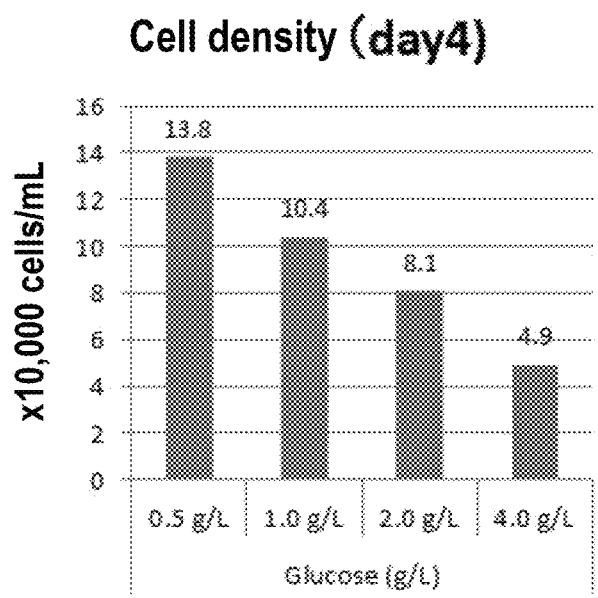

[Fig. 16]
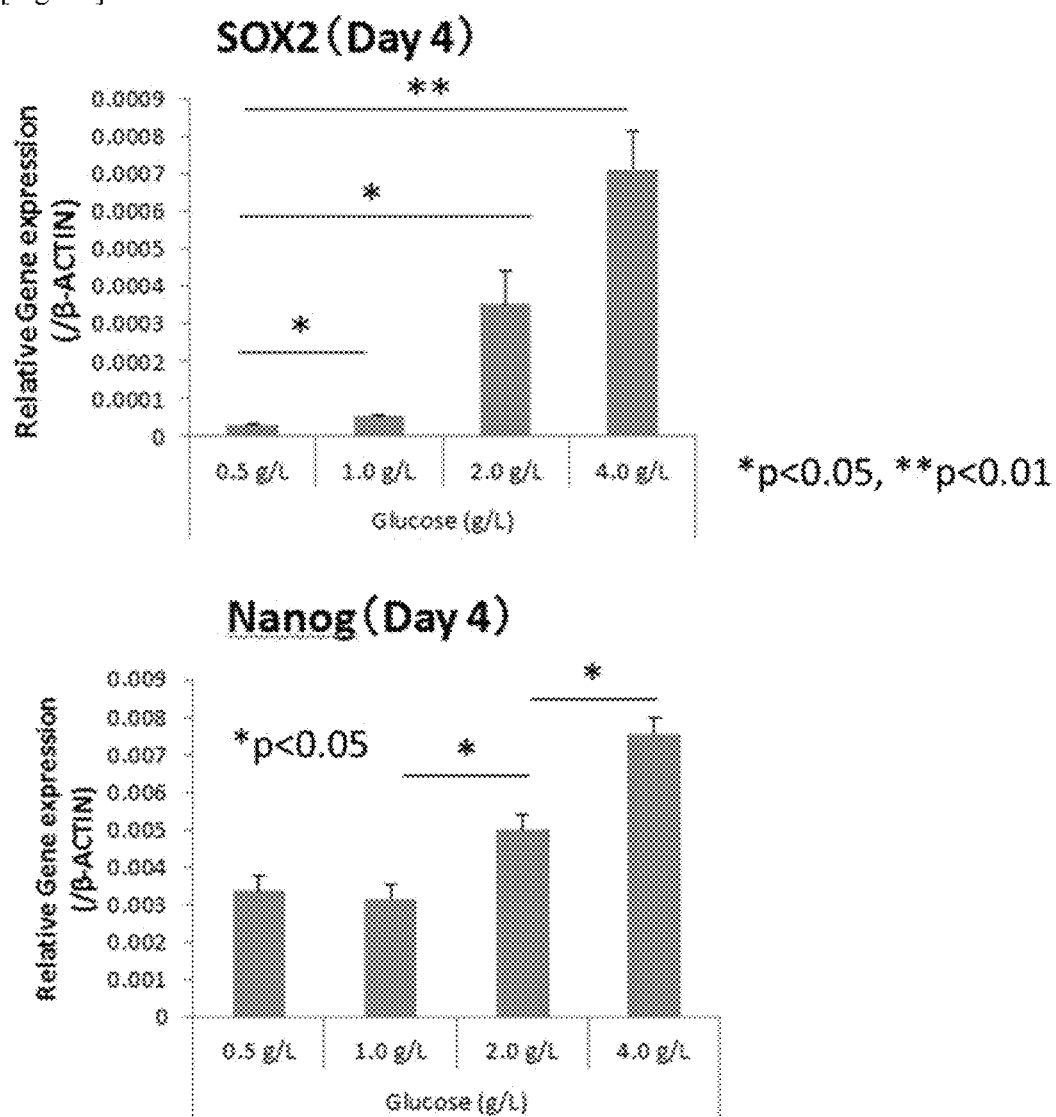

[Fig. 17]
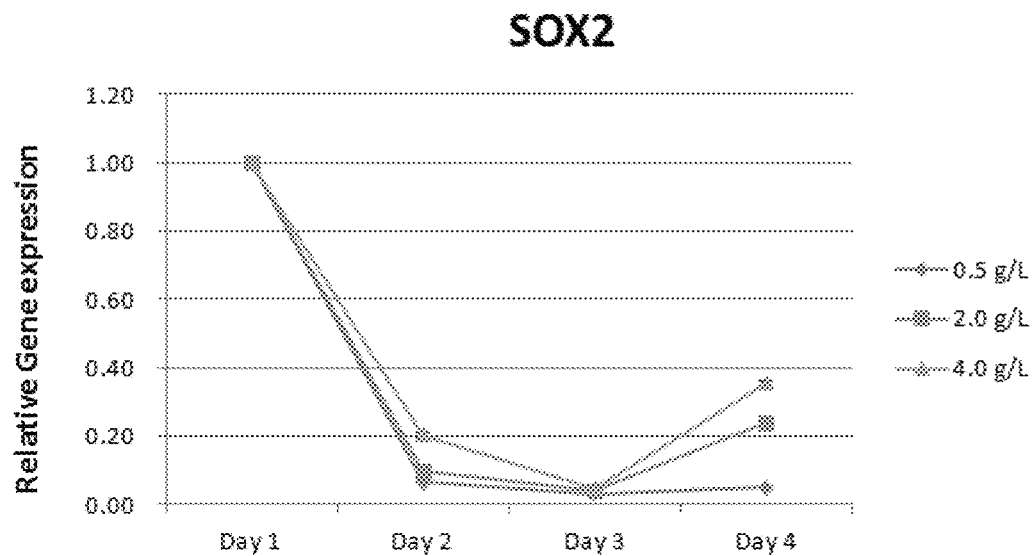
[Fig. 18]
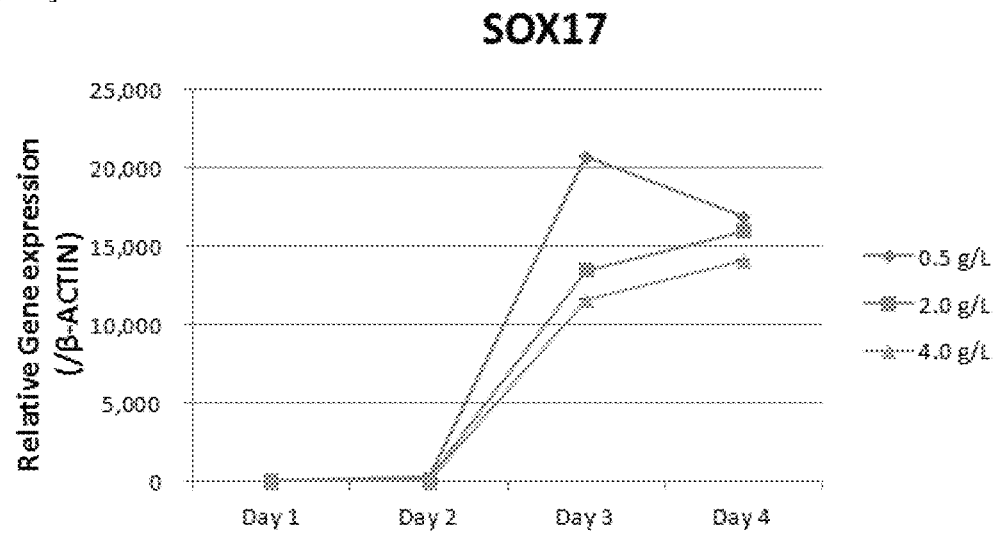

[Fig. 19]
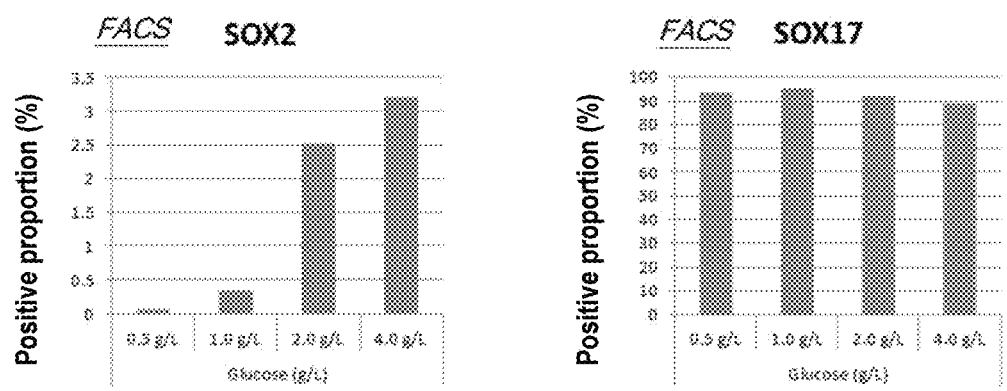
[Fig. 20]
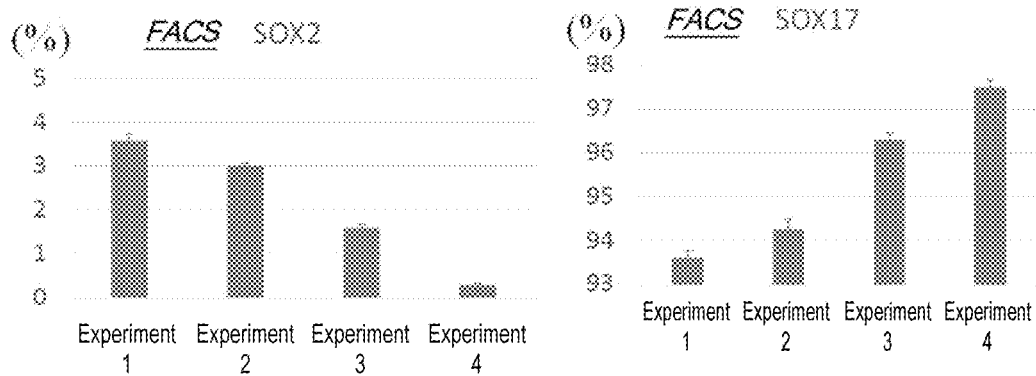

[Fig. 21]
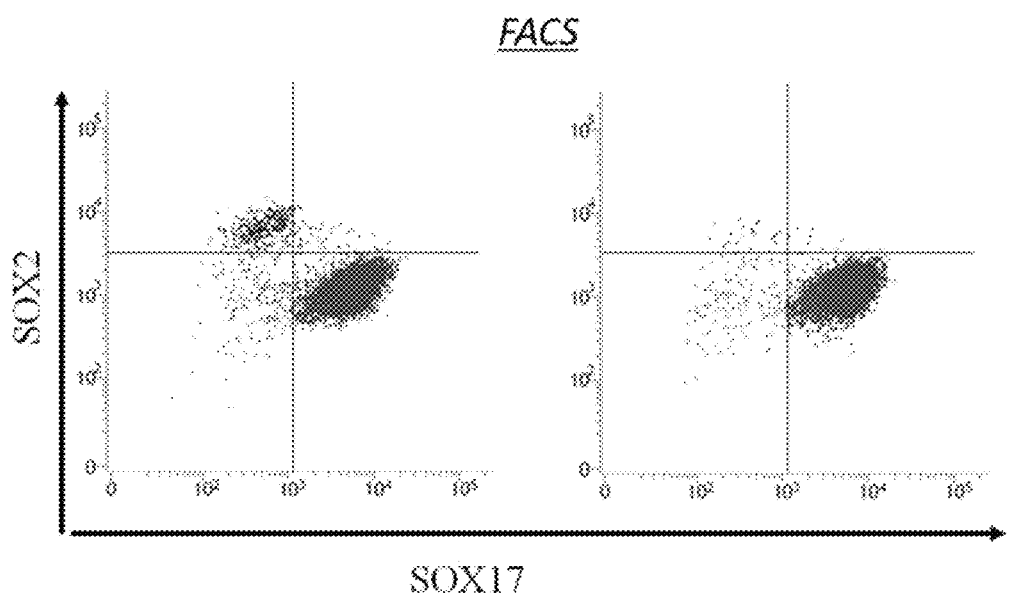

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 1
gtctccacac atcagcacaa ctac                                          24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
ttcggttgtt gctgatctgt c                                             21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
gagatcctcc gacaattcaa cc                                            22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 4
aaacagcagc tgatcctgac tg                                            22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
aagagatcca tggtgttcaa ggac                                          24

<210> SEQ ID NO 6
<211> LENGTH: 24
<212> TYPE: DNA
<213> ORGANISM: Artificial Sequence
<220> FEATURE:
```

```
<223> OTHER INFORMATION: Description of Artificial Sequence: primer

<400> SEQUENCE: 6
aggtaggcat actcattgtc atcg                                              24

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
cgaagaatag caatggtgtg ac                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 8
gttgctccag gttgaattgt tc                                                22

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 9
gtcagaggga tcacaatctt tcag                                              24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 10
gtcttgtcgt tggacgttag ttc                                               23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 11
cgcttcaaga acatgtgtaa gctgc                                             25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 12
ctctcactcg gttctcgata ctg                                               23
```

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 13
ataagtactg gcgaaccatc tctg                                          24

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 14
aattaccaac ggtgtcaacc tg                                            22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 15
atgatcctga ctgcgatgag ag                                            22

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 16
cagtgtcctt gtctgttctt ctgac                                         25

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 17
gtcaccttcg tgaataccaa gac                                           23

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 18
aggcagagaa atcctgctct c                                             21

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: primer
```

<400> SEQUENCE: 19
gtcagaggga tcacaatctt tcag                                              24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 20
gtcttgtcgt tggacgttag ttc                                               23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 21
cgcttcaaga acatgtgtaa gctgc                                             25

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 22
ctctcactcg gttctcgata ctg                                               23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 23
tacacacttc ctggaggagc taag                                              24

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 24
ccaaactgtt caagtggcag ac                                                22

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 25
gagatctacc agtggatcat ggac                                              24

<210> SEQ ID NO 26
<211> LENGTH: 22

```
<212> TYPE: DNA
<213> ORGANISM: Artificial Sequence
<220> FEATURE:
<223> OTHER INFORMATION: Description of Artificial Sequence: primer

<400> SEQUENCE: 26
caccttcagg aaacagtcgt tg                                              22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 27
ctctgtcaac gaaggcttga ac                                              22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 28
cacttccaaa gcctaagcac tg                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 29
atagaagggc acgtggtgat tc                                              22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 30
atgtgtcata ctgggaggtg ttg                                             23

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 31
ccgcacgatt tcattgaac                                                  19

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 32
```

```
acttcacatc tgtggcacag ag                                                  22

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 33
cacccattta cacctacacc aag                                                 23

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 34
ttgcagatct caggagtgac ag                                                  22

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 35
gtttcatctc ctcggatgag tatg                                                24

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 36
tagttgctta gctcctcctc acc                                                 23
```

ENDODERMAL CELL POPULATION, AND METHOD FOR PRODUCING CELL POPULATION OF ANY OF THREE GERM LAYERS FROM PLURIPOTENT CELL

REFERENCE TO SEQUENCE LISTING SUBMITTED VIA EFS-WEB

This application includes an electronically submitted sequence listing in .txt format. The .txt file contains a sequence listing entitled "2021-08-03_1609-1365PUS1_ST25.txt" created on Aug. 3, 2021 and is 8,126 bytes in size. The sequence listing contained in this .txt file is part of the specification and is hereby incorporated by reference herein in its entirety.

TECHNICAL FIELD

The present invention relates to an endodermal cell population. The present invention further relates to a method for producing a cell population of any of three germ layers by culturing a pluripotent stem cell and inducing the cell to differentiate thereinto.

BACKGROUND ART

Regenerative medicine draws great expectations in an alternative method of an organ transplantation which suffers from a donor shortage issue, a new therapy development for intractable diseases, and the like. Embryonic stem cells (ES cells) and induced pluripotent stem cells (iPS cells) have pluripotency and infinite proliferative capacity, and are thus expected to be cell sources for preparing cells required for the regenerative medicine. When the regenerative medicine using these pluripotent stem cells is practiced, a technique for effective differentiation induction of a pluripotent stem cell into a target cell needs to be established, and various differentiation induction methods are reported.

For example, as a culture method for inducing differentiation of a pluripotent stem cell into any of three germ layers, Non-Patent Document 1 discloses that human ES cells and human iPS cells are induced to differentiate into three germ layers (endodermal cell, ectodermal cell, or mesodermal cell) while adhesively cultured on a petri dish coated with Matrigel™. Further, the differentiation induction efficiency is also described to be enhanced when the culture is carried out for 10 hours in a methionine-free medium before differentiation induction to arrest the cell cycle and subsequently the differentiation into three germ layers (endodermal cell, ectodermal cell, or mesodermal cell) is induced.

Also reported are some findings on media for inducing differentiation of a pluripotent stem cell into endodermal cells.

For example, Patent Document 1 discloses that a TGFβ superfamily growth factor is supplied to a pluripotent cell culture to carry out the differentiation into a definitive endoderm, and subsequently TGFβ superfamily growth factor signal transduction is reduced, eliminated, or removed in a cell culture or a cell population of SOX17-positive definitive endodermal cells thereby to differentiate the definitive endodermal cells into PDX1-negative foregut endodermal cells (paragraphs 0144 to 0150).

Further, Patent Document 2 discloses a method for differentiating a pluripotent cell into hemopoietic precursor cells or endothelial cells, the method comprises the following sequential steps: (a) a step of culturing or maintaining a plurality of substantially undifferentiated pluripotent cells in a first specific medium containing at least one growth factor, (b) a step of incubating the cells in a second specific medium essentially free of BMP4, VEGF, IL-3, Flt3 ligand, and GMCSF, (c) a step of culturing the cells in a third specific medium containing BMP4 and VEGF in sufficient amounts to promote the proliferation or differentiation of a plurality of the cells, and (d) a step of culturing the cells in a fourth specific medium containing any of (1) IL-3 and Flt3 ligand, or (2) VEGF, FGF-2 or FGF-2 mimetic, and IGF in sufficient amounts to promote the proliferation or differentiation of a plurality of the cells, whereby a plurality of the pluripotent cells differentiate into hemopoietic precursor cells or endothelial cells (paragraph 0009).

PRIOR ART DOCUMENTS

Patent Documents

Patent Document 1: JP Patent Publication (Kohyo) No. 2016-506736 A
Patent Document 2: JP Patent Publication (Kokai) No. 2015-192681 A

Non-Patent Document

Non-Patent Document 1: Shiraki N et al., Methionine metabolism regulates maintenance and differentiation of human pluripotent stem cells. Cell Metab. 2014 May 6; 19(5):780-94.

SUMMARY OF INVENTION

Object to be Solved by the Invention

As described above, culture methods for inducing differentiation of pluripotent stem cells into any of somatic cells through three germ layers (endodermal cell, ectodermal cell, or mesodermal cell) have been reported, however, from the viewpoints of enhancing therapeutic effects as a cell therapy preparation and reducing undifferentiated cells, the differentiation induction efficiency needs to be further enhanced and the quality of cells needs to be increased.

Accordingly, an object to be solved by the present invention is to provide an endodermal cell population for obtaining optimal somatic cells as cell therapy preparations. A further object to be solved by the present invention is to provide a method for producing a cell population of any of three germ layers which comprises culturing a pluripotent stem cell, wherein a content proportion of undifferentiated cells in the cell population is reduced and a cell population which is differentiable into optimal somatic cells as cell therapy preparations can be obtained.

Means for Solving the Object

The present inventors conducted extensive studies to solve the above objects and found that the differentiation induction efficiency into endodermal cells can be significantly enhanced when pluripotent stem cells are subjected to suspension culture with a specific compound added or not added before induced to differentiate and, for the differentiation induction, factors causing the differentiation induction are added, reduced, eliminated, or removed. Further, the present inventors found that, in the aspect that the somatic cells which were obtained by differentiation induction from the obtained endodermal cell population exhibit higher therapeutic effects, such an endodermal cell population is more excellent than the conventional endodermal cell populations. The present invention was accomplished based on these findings.

More specifically, according to the present description, the following inventions are provided.

(1) An endodermal cell population, wherein a relative expression level of a Nanog gene to an expression level of an OAZ1 gene is 0.8 or less, a relative expression level of a HNF1B gene to an expression level of the OAZ1 gene is 1.0 or more, and a proportion of SOX17-positive cells is 80% or more.
(2) The endodermal cell population according to (1), wherein a relative expression level of a HNF4A gene to an expression level of the OAZ1 gene is 0.5 or more.
(3) The endodermal cell population according to (1) or (2), wherein a relative expression level of an EpCAM gene to an expression level of the OAZ1 gene is 0.6 or more.
(4) The endodermal cell population according to any one of (1) to (3), wherein a relative expression level of a VIM gene to an expression level of the OAZ1 gene is 12 or less.
(5) The endodermal cell population according to any one of (1) to (4), wherein a relative expression level of a SOX2 gene to an expression level of the OAZ1 gene is 0.11 or less.
(6) The endodermal cell population according to any one of (1) to (5), wherein a relative expression level of a c-Myc gene to an expression level of the OAZ1 gene is 0.1 or less.
(7) The endodermal cell population according to any one of (1) to (6), wherein a relative expression level of a Fibronectin-1 gene to an expression level of the OAZ1 gene is 1.0 or more.
(8) The endodermal cell population according to any one of (1) to (7), wherein a relative expression level of a Cyclin D1 gene to an expression level of the OAZ1 gene is 0.015 or less.
(9) The endodermal cell population according to any one of (1) to (8), wherein a relative expression level of a Matrix metallopeptidase 2 gene to an expression level of the OAZ1 gene is 0.020 or less.
(10) A method for producing an endodermal cell from a pluripotent stem cell, the method comprising the following (a) to (b):
(a) a step of suspension culture of a pluripotent stem cell using a medium containing 2-mercaptoethanol to prepare a cell population, and
(b) a step of culturing the cell population using a medium containing a TGFβ superfamily signaling activator, and subsequently culturing using a medium to which FGF2 and BMP4 are not added.
(11) The production method according to (10), wherein, to the medium containing 2-mercaptoethanol, activin A is not added.
(12) The production method according to (10) or (11), wherein, to the medium containing 2-mercaptoethanol, a WNT signaling activator is not added.
(13) The production method according to any one of (10) to (12), wherein, to the medium containing 2-mercaptoethanol, FGF2 is not added.
(14) The production method according to any one of (10) to (13), wherein, to the medium containing 2-mercaptoethanol, TGFβ1 is not added.
(15) The production method according to any one of (10) to (14), wherein the medium containing 2-mercaptoethanol further contains insulin.
(16) The production method according to any one of (10) to (15), wherein the medium to which FGF2 and BMP4 are not added contains at least one selected from the group consisting of insulin, transferrin, sodium selenite, and ethanolamine.
(17) The method according to any one of (10) to (16), wherein the medium containing a TGFβ superfamily signaling activator and/or the medium to which FGF2 and BMP4 are not added further contains 2-mercaptoethanol.
(18) The method according to any one of (10) to (17), wherein the medium containing a TGFβ superfamily signaling activator and/or the medium to which FGF2 and BMP4 are not added contains glucose in a concentration of 1.0 g/L or less.
(19) A method for producing a cell population of any of three germ layers from a pluripotent stem cell, the method comprising the following (a) to (b):
(a) a step of suspension culture of a pluripotent stem cell using a medium containing 2-mercaptoethanol to prepare a cell population, and
(b) a step of culturing the cell population under conditions that allow the cell population to be induced to differentiate into any of an endodermal cell, a mesodermal cell, or an ectodermal cell.
(20) The production method according to (19), wherein, to the medium containing 2-mercaptoethanol, FGF2 is not added.
(21) The production method according to (19) or (20), wherein, to the medium containing 2-mercaptoethanol, TGFβ1 is not added.

Advantageous Effects of Invention

An endodermal cell population of the present invention has a reduced content proportion of undifferentiated cells in the cell population and includes endodermal cells differentiable into optimal somatic cells as cell therapy preparations. Further, a somatic cell derived from the endodermal cell population of the present invention has good therapeutic effects as a cell therapy preparation. Furthermore, a production method of the present invention can reduce a content proportion of undifferentiated cells in a cell population and provide a cell population differentiable into optimal somatic cells as cell therapy preparations, whereby a high quality cell therapy preparation can be provided.

BRIEF DESCRIPTION OF DRAWINGS

FIG. 1 shows analysis results on the expression of undifferentiation markers and primitive gut tube (PGT) markers in adhesion culture and suspension culture of pluripotent stem cells.

FIG. 2 shows analysis results on the expression of SOX17 in adhesion culture and suspension culture of pluripotent stem cells.

FIG. 3 shows analysis results on the expression of EpCAM and VIM in adhesion culture and suspension culture of pluripotent stem cells.

FIG. 4 shows measurement results on c-peptide concentrations in blood in cell transplantation experiment of diabetes model mice.

FIG. 5 shows measurement results on casual blood glucose levels in cell transplantation experiment of diabetes model mice.

FIG. 6 shows measurement results on expression levels of OCT4, SOX17, and FOXA2 in the differentiation induction of human iPS cells into endodermal cells.

FIG. 7 shows measurement results on SOX2- and SOX17-positive cell proportions in the differentiation induction of human iPS cells into endodermal cells.

FIG. 8 shows cell densities on Day 5 in the differentiation induction of human iPS cells into endodermal cells.

FIG. 9 shows measurement results on SOX17- and FOXA2-positive cell proportions in the differentiation induction of human iPS cells into endodermal cells.

FIG. 10 shows analysis results on the expression of Fibronectin-1 (FN1) in adhesion culture and suspension culture of pluripotent stem cells.

FIG. 11 shows analysis results on the expression of Cyclin D1 in adhesion culture and suspension culture of pluripotent stem cells.

FIG. 12 shows analysis results on the expression of CD44 in adhesion culture and suspension culture of pluripotent stem cells.

FIG. 13 shows analysis results on the expression of matrix metallopeptidase 2 (MMP2) in adhesion culture and suspension culture of pluripotent stem cells.

FIG. 14 shows analysis results on the expression of insulin receptor substrate 1 (IRS1) in adhesion culture and suspension culture of pluripotent stem cells.

FIG. 15 shows cell densities in the case where pluripotent stem cells are induced to differentiate in different glucose concentrations.

FIG. 16 shows analysis results on the expression of SOX2 and Nanog in the case where pluripotent stem cells are induced to differentiate in different glucose concentrations.

FIG. 17 shows analysis results on the expression of SOX2 in the case where pluripotent stem cells are induced to differentiate in different glucose concentrations.

FIG. 18 shows analysis results on the expression of SOX17 in the case where pluripotent stem cells are induced to differentiate in different glucose concentrations.

FIG. 19 shows measurement results on the SOX2- and SOX17-positive proportions in the case where pluripotent stem cells are induced to differentiate in different glucose concentrations.

FIG. 20 shows measurement results on the SOX2- and SOX17-positive proportions in the case where pluripotent stem cells are induced to differentiate in different glucose concentrations.

FIG. 21 shows analysis results on the expression of SOX2 and SOX17 in the case where pluripotent stem cells are induced to differentiate in different glucose concentrations.

EMBODIMENTS FOR CARRYING OUT THE INVENTION

Hereinafter, embodiments of the present invention will be specifically described, but the following description is to help understand the present invention easily and the scope of the present invention is not limited to the following embodiments, and other embodiments suitably substituted with an element of the following embodiments by a person skilled in the art are also encompassed in the scope of the present invention.

The term "is not added" used for a medium of the present invention refers that a factor such as a protein, a peptide, and a compound specified as not added to a culture or conditioned medium are not exogenously added. Note that when a factor such as a protein, a peptide, and a compound specified as not added to a culture or conditioned medium are brought in due to the continuous culture operation, such a factor is adjusted to be less than 1% (volume/volume), less than 0.5% (volume/volume), less than 0.1% (volume/volume), less than 0.05% (volume/volume), less than 0.01% (volume/volume), or less than 0.001% (volume/volume).

The term "is reduced" used for a cell population of the present invention means that a cell type (may also be a positive or negative proportion of a cell surface marker) specified as not contained in a cell population is present in an amount, in the total number of cell populations, less than 30%, less than 20%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, or less than 0.1%.

The term "is enhanced" used for a gene expression level of the present invention refers that an expression of a gene is more increased than a specific gene expression level in a cell population to be compared, and is, against a cell population to be compared, 1.1 times or more, 1.2 times or more, 1.3 times or more, 1.4 times or more, 1.5 times or more, 1.6 times or more, 1.7 times or more, 1.8 times or more, 1.9 times or more, 2.0 times or more, 2.1 times or more, 2.2 times or more, 2.3 times or more, 2.4 times or more, 2.5 times or more, 2.6 times or more, 2.7 times or more, 2.8 times or more, 2.9 times or more, 3.0 times or more, 3.1 times or more, 3.2 times or more, 3.3 times or more, 3.4 times or more, 3.5 times or more, 3.6 times or more, 3.7 times or more, 3.8 times or more, 3.9 times or more, 4.0 times or more, 4.1 times or more, 4.2 times or more, 4.3 times or more, 4.4 times or more, 4.5 times or more, 4.6 times or more, 4.7 times or more, 4.8 times or more, 4.9 times or more, 5.0 times or more, 5.1 times or more, 5.2 times or more, 5.3 times or more, 5.4 times or more, 5.5 times or more, 5.6 times or more, 5.7 times or more, 5.8 times or more, 5.9 times or more, 6.0 times or more, 6.1 times or more, 6.2 times or more, 6.3 times or more, 6.4 times or more, 6.5 times or more, 6.6 times or more, 6.7 times or more, 6.8 times or more, 6.9 times or more, 7.0 times or more, 7.1 times or more, 7.2 times or more, 7.3 times or more, 7.4 times or more, 7.5 times or more, 7.6 times or more, 7.7 times or more, 7.8 times or more, 7.9 times or more, 8.0 times or more, 8.1 times or more, 8.2 times or more, 8.3 times or more, 8.4 times or more, 8.5 times or more, 8.6 times or more, 8.7 times or more, 8.8 times or more, 8.9 times or more, 9.0 times or more, 9.1 times or more, 9.2 times or more, 9.3 times or more, 9.4 times or more, 9.5 times or more, 9.6 times or more, 9.7 times or more, 9.8 times or more, 9.9 times or more, or 10.0 times or more.

The term "is reduced" used for a gene expression level of the present invention refers that an expression of a gene is more reduced than a specific gene expression level in a cell population to be compared, and is, against a cell population to be compared, 1.1 times or less, 1.2 times or less, 1.3 times or less, 1.4 times or less, 1.5 times or less, 1.6 times or less, 1.7 times or less, 1.8 times or less, 1.9 times or less, 2.0 times or less, 2.1 times or less, 2.2 times or less, 2.3 times or less, 2.4 times or less, 2.5 times or less, 2.6 times or less, 2.7 times or less, 2.8 times or less, 2.9 times or less, 3.0 times or less, 3.1 times or less, 3.2 times or less, 3.3 times or less, 3.4 times or less, 3.5 times or less, 3.6 times or less, 3.7 times or less, 3.8 times or less, 3.9 times or less, 4.0 times or less, 4.1 times or less, 4.2 times or less, 4.3 times or less, 4.4 times or less, 4.5 times or less, 4.6 times or less, 4.7 times or less, 4.8 times or less, 4.9 times or less, 5.0 times or less, 5.1 times or less, 5.2 times or less, 5.3 times or less, 5.4 times or less, 5.5 times or less, 5.6 times or less, 5.7 times or less, 5.8 times or less, 5.9 times or less, 6.0 times or less, 6.1 times or less, 6.2 times or less, 6.3 times or less, 6.4 times or less, 6.5 times or less, 6.6 times or less, 6.7 times or less, 6.8 times or less, 6.9 times or less, 7.0 times or less, 7.1 times or less, 7.2 times or less, 7.3 times or less, 7.4 times or less, 7.5 times or less, 7.6 times or less, 7.7 times or less, 7.8 times or less, 7.9 times or less, 8.0 times or less, 8.1 times or less, 8.2 times or less, 8.3 times or less, 8.4 times or less, 8.5 times or less, 8.6 times or less, 8.7 times or less, 8.8 times or less, 8.9 times or less, 9.0 times or less, 9.1 times or less, 9.2 times or less, 9.3 times or less, 9.4 times or less, 9.5 times or less, 9.6 times or less, 9.7 times or less, 9.8 times or less, 9.9 times or less, 10.0 times or less, 20 times or less, 30 times or less, 40 times or less, 50 times or less, 60 times or less, 70 times or less, 80 times or less, 90 times or less, 100 times or less, 250 times or less, 500 times or less, 750 times or less, 1000 times or less, 5000 times or less, or 10000 times or less.

An aggregate of the present invention can be used interchangeably with the term "clump" or "cluster", and generally refers to a group of cells which are not dissociated into single cells.

[1] Pluripotent Stem Cell

In a production method of the present invention, cell populations of three germ layers (endodermal cells, mesodermal cells or ectodermal cells) are produced by culturing pluripotent stem cells.

The pluripotent stem cells mean cells which can differentiate into all the types of cells constituting the living body, have multilineage differentiation potential (pluripotency), and continue proliferation infinitely while maintaining pluripotency in vitro under suitable conditions. Specific examples thereof include embryonic stem cells (ES cells), pluripotent stem cells derived from embryonic primordial germ cells (EG cells, Proc Natl Acad Sci USA. 1998, 95: 13726-31), pluripotent stem cells derived from the spermary (GS cells, Nature. 2008, 456: 344-9), induced pluripotent stem cells (iPS cells) and somatic stem cells (tissue stem cells). The pluripotent stem cells are preferably iPS cells or ES cells, and are more preferably iPS cells. The "embryos (embryonic)" also refer to embryos derived by somatic nucleus transplantation in addition to embryos derived by syngamy.

As the ES cells, cells derived from any warm-blooded animals, preferably mammals, can be used. Examples of the mammals include mice, rats, guinea pigs, hamsters, rabbits, cats, dogs, sheep, swine, bovines, horses, goats, simians or humans. Cells derived from humans can be preferably used.

Specific examples of the ES cells include ES cells of mammals or the like established by culturing early embryos before implantation, ES cells established by culturing early embryos produced by the transplantation of the somatic nuclei, and ES cells obtained by modifying genes on chromosomes of these ES cells using techniques of genetic engineering. The ES cells can be prepared according to methods usually performed in the field and publicly known documents. ES cells of mice have been established by Evans et al. (Evans et al., 1981, Nature 292: 154-6) and Martin et al. (Martin G R. et al., 1981, Proc Natl Acad Sci 78: 7634-8) in 1981. Human ES cells have been established by Thomson et al. (Thomson et al., Science, 1998, 282: 1145-7) in 1998, are available from WiCell Research Institute (website: http://www.wicell.org/, Madison, Wis., the United States of America), the National Institute of Health, Kyoto University or the like, and can be purchased, for example, from Cellartis (website: http://www.cellartis.com/, Sweden).

Induced pluripotent stem cells (iPS cells) are cells having pluripotency and obtained by reprogramming somatic cells.

A plurality of groups including the group of the professor Shinya Yamanaka et al. of Kyoto University, the group of Rudolf Jaenisch et al. of Massachusetts Institute of Technology, the group of James Thomson et al. of University of Wisconsin, the group of Konrad Hochedlinger et al. of Harvard University, and the like have succeeded in creating iPS cells. For example, International Publication No. WO 2007/069666 describes a somatic nucleus reprogramming factor containing the gene products of an Oct family gene, a Klf family gene and a Myc family gene as well as a somatic nucleus reprogramming factor containing the gene products of an Oct family gene, a Klf family gene, a Sox family gene and a Myc family gene, and further describes a method for producing induced pluripotent stem cells by reprogramming somatic nuclei, comprising a step of contacting somatic cells with the nucleus reprogramming factors.

The type of somatic cells used for producing iPS cells is not particularly limited, and any somatic cells can be used. That is, the somatic cells include all the cells other than reproductive cells among cells constituting the living body, may be differentiated somatic cells or undifferentiated stem cells. The origin of somatic cells may be any of mammals, birds, fish, reptiles, and amphibians, and it is not particularly limited. However, it is preferably mammals (for example, rodents such as mice; or primates such as humans), and is particularly preferably mice or humans. When human somatic cells are used, somatic cells of any of an unborn baby, a newborn, or an adult may be used. Specific examples of the somatic cells include fibroblasts (for example, dermal fibroblasts), epithelial cells (for example, gastric epithelial cells, liver epithelial cells and alveolar epithelial cells) and endothelial cells (for example, blood vessels and lymph vessels), nerve cells (for example, neurons and glial cells), pancreas cells, white blood cells (B cells, T cells and the like), marrow cells, muscle cells (for example, skeletal muscle cells, smooth muscle cells, and cardiac muscle cells), hepatic mesenchymal cells, non-hepatic mesenchymal cells, adipose cells, osteoblasts, cells constituting parodontium (for example, periodontal membrane cells, cementoblasts, gingival fibroblasts and osteoblasts) and cells constituting the kidneys, the eyes and the ears.

iPS cells are stem cells having self-replicating capability over a long period of time under predetermined culture conditions (for example, under the conditions for culturing ES cells) and having multipotency, which enables differentiation into any of ectodermal cells, mesodermal cells and endodermal cells, under predetermined differentiation induction conditions. When iPS cells are transplanted to test animals such as mice, they may be stem cells having the capability to form teratomas.

To produce iPS cells from somatic cells, at least one or more reprogramming genes are first introduced into the somatic cells. The reprogramming genes are genes encoding reprogramming factors having the function of reprogramming somatic cells and making them iPS cells. Specific examples of the combination of reprogramming genes include the following combinations, but are not limited to these.

(i) An Oct gene, a Klf gene, a Sox gene, and a Myc gene
(ii) An Oct gene, a Sox gene, a NANOG gene, and a LIN28 gene
(iii) An Oct gene, a Klf gene, a Sox gene, a Myc gene, a hTERT gene, and a SV40 large T gene
(iv) An Oct gene, a Klf gene, and a Sox gene A method in which transgenes are further reduced (Nature. 2008 Jul. 31; 454 (7204): 646-50), a method using a low molecular weight compound (Cell Stem Cell. 2009 Jan. 9; 4(1): 16-9, Cell Stem Cell. 2009 Nov. 6; 5(5): 491-503), a method using transcription factor proteins instead of genes (Cell Stem Cell. 2009 May 8; 4(5): 381-4), and the like have been reported besides the above, and the iPS cells may be iPS cells produced by any method.

[2] Three Germ Layers

According to a method of the present invention, the cell population of any of three germ layers such as endodermal cells, ectodermal cells, and mesodermal cells is produced from pluripotent stem cells.

Examples of the three germ layers include endodermal cells, mesodermal cells, and ectodermal cells.

The endodermal cells have the capability to differentiate into tissues of organs such as the alimentary canal, the lungs, the thyroid gland, the pancreas and the liver; cells of the secretory glands having an opening to the alimentary canal; the peritoneum; the pleura; the larynx; the auditory tubes; the trachea; the bronchi; the urinary tract (the bladder, most of the urethra, and a part of the ureters); or the like, and may be generally called an definitive endoderm (DE). The differentiation into endodermal cells from pluripotent stem cells can be confirmed by measuring the expression levels of genes specific to endodermal cells. Examples of the genes specific to endodermal cells include SOX17, FOXA2, CXCR4, AFP, GATA4, and EOMES. The endodermal cells may be called the definitive endoderm and used herein.

Mesodermal cells differentiate into a coelom and the mesothelium backing it; the muscles; the skeleton; the skin derma; connective tissue; the heart; the blood vessels (also including the vascular endothelium); blood (also including the blood cells); the lymph vessels; the spleen; the kidneys; the ureters; the genital glands (the spermaries, the womb, the genital gland epitheliums); or the like. Examples of the genes specific to mesodermal cells include MESP1, MESP2, FOXF1, BRACHYURY, HAND1, EVX1, IRX3, CDX2, TBX6, MIXL1, ISL1, SNAI2, FOXC1, and PDGFRα.

Ectodermal cells form the cuticle of the skin, the epithelium of the male urethra end piece, the hairs, the nails, the dermal glands (including the mammary glands and the sweat glands), the sense organs (including the epithelium of the end pieces of the oral cavity, the pharynx, the nose and the rectum; and the salivary glands), the crystalline lenses, or the like. Some of the ectodermal cells invaginate in the shape of a vallecula in the developmental process and form a neural tube. The neurons of the central nervous system such as the brain and the spinal cord; or the melanocytes are derived from the ectodermal cells. The peripheral nervous system is also formed. Examples of the genes specific to ectodermal cells include FGF5, OTX2, SOX1, and PAX6.

Although three germ layer cell populations produced by a method of the present invention may be any of an endodermal cell population, a mesodermal cell population, or an ectodermal cell population, and are particularly preferably an endodermal cell population.

According to the method of the present invention, somatic cells which can be used for the treatment of the alimentary system such as the pancreas, the liver, the stomach, and the intestines can be obtained using an endodermal cell population induced to differentiate from pluripotent stem cells. Although one of embodiments in the treatment of digestive organs is illustrated below, the present invention is not limited to this.

In the case of the intestine system, when intestine precursor cells such as crypt cells are obtained, these can be used for the treatment of ulcerative colitis, Crohn disease, a short intestine symptom or the like by transplanting these with a catheter or the like.

In the case of the pancreas system, when pancreatic β cells (occasionally called insulin-producing cells) are obtained, these can be used for the treatment of diabetes by transplanting these with a catheter or the like, or sealing these in an immunoisolating device or the like and transplanting these.

In the case of the liver system, for example, when albumin-producing cells are obtained, these can be used for the treatment of external injury accompanied with massive hemorrhage, or the like by transplanting these with a catheter or the like, or sealing these in an immunoisolating device and transplanting them.

Tissues for treatment in the alimentary system such as the pancreas, the liver, the stomach, and the intestines can also be obtained by culturing using a polymer support carrier or the like. For example, when liver tissue is obtained by induction, it can be used for the treatment of liver cancer, liver cirrhosis, acute hepatic failure, and liver metabolic disorder such as hemochromatosis. When lung cellular tissue is obtained, it can be used for the treatment of lung respiratory organ diseases such as cystic fibrosis and asthma by transplanting this to the affected part. In the case of the kidney system, when tissue containing mesangial cells, renal tubular epithelial cells, glomerular cells or the like is obtained, it can be used for the treatment of renal insufficiency and nephritis; dialysis treatment; or the like by transplanting this directly. Liver system cells enabling metabolism are obtained, albumin-generating cells, blood coagulation factor-generating cells and cells generating a metabolizing enzyme such as al antitrypsin are created, and the generated metabolizing enzyme can be used for the treatment of the deficiency disease of these proteins by directly injecting or intravenously dripping it. For example, pancreas system cells such as pancreatic β cells enabling metabolism are obtained, insulin generated by the pancreatic β cells is directly injected, and can be used for the treatment of type I diabetes.

A cell population of any of three germ layers obtained by the method of the present invention and somatic cells obtained therefrom can also be used for evaluating the medicinal effects/toxicity of test substances, clarifying the effect mechanisms and analyzing life phenomenon mechanisms.

[3] Maintenance Culture of Pluripotent Stem Cells

The undifferentiating state of pluripotent stem cells before the pluripotent stem cells are induced to differentiate according to the method of the present invention is preferably maintained by using an undifferentiation-maintaining medium. Culture in which the undifferentiating state of pluripotent stem cells is maintained by using an undifferentiation-maintaining medium is also called the maintenance culture of pluripotent stem cells.

The undifferentiation-maintaining medium is not particularly limited as long as it is a medium which enables to maintain the undifferentiating state of pluripotent stem cells. Examples thereof however include a medium containing a leukemia inhibitory factor wherein it is known that the leukemia inhibitory factor has a property of maintaining the undifferentiating state of mouse embryonic stem cells and mouse induced pluripotent stem cells; and a medium containing a basic FGF (fibroblast growth factor) wherein it is known that the basic FGF has a property of maintaining the undifferentiating state of human iPS cells. Although, for example, a human iPS cell medium [a DMEM-Ham's F12

(Wako Pure Chemical Corporation) containing 20% Knock-Out Serum Replacement (KSR; Gibco), 1×Non-Essential Amino Acids (NEAA; Wako Pure Chemical Corporation), 55 µmol/L 2-mercaptoethanol (2-ME; Gibco), 7.5 ng/mL recombinant human fibroblast growth factor 2 (FGF 2; PeproTech, Inc.) and 0.5×Penicillin and Streptomycin (PS; Wako Pure Chemical Corporation)]; an Essential 8™ medium (Thermo Fisher Scientific K.K.); a STEMPRO (registered trademark) hESC SFM (Life Technologies Japan Ltd.); a mTeSR1 (VERITAS Corporation); a TeSR2 (VERITAS Corporation); a StemFit (registered trademark); or the like can be used, and the undifferentiation-maintaining medium is not particularly limited.

The maintenance culture of pluripotent stem cells can be performed on suitable feeder cells (for example, SL10 feeder cells, SNL feeder cells or the like) using the above-mentioned undifferentiation-maintaining media. The maintenance culture of pluripotent stem cells can be performed using the above-mentioned undifferentiation-maintaining media on cell culture dishes coated with a cell adhesion protein or an extracellular matrix such as vitronectin, fibronectin, laminin, collagen or Matrigel™.

The culture temperature is not particularly limited as long as it is a culture temperature suitable for the culture of pluripotent stem cells to be used. However, it is generally 30° C. to 40° C., and preferably around 37° C.

It is preferable to perform culture in an atmosphere at a $CO_2$ concentration of around 1 to 10%, preferably 5%, using a $CO_2$ incubator or the like.

Maintenance culture of pluripotent stem cells can be performed with subculturing for a desired period of time, and it is preferred to perform aggregate formation and differentiation induction by using pluripotent stem cells after 1 to 100 passages, preferably after 10 to 50 passages, more preferably after 25 to 40 passages from the initiation of maintenance culture.

[4] Aggregate Formation Through Suspension Culture of Pluripotent Stem Cells

In one of embodiments to form an aggregate of pluripotent stem cells, undifferentiated cells under maintenance culture are detached from feeder cells by using CTK Solution (Dissociation Solution for human ES/iPS Cells: ReproCELL Inc.) or the like, and the feeder cells can be then removed by rinsing three or four times with a medium for human iPS cells. Subsequently, the resulting cells are crushed by pipetting into smaller cell clumps or single cells, which are suspended in a medium and then subjected to suspension culture with stirring or rotating until the pluripotent stem cells in the suspension form an aggregate.

The suspension culture may be based on static culture using viscosity or the like of a medium or a microwell or the like including concaves and convexes, or culture under conditions such that a liquid medium flows with use of a spinner or the like; however, the suspension culture is preferably based on culture under conditions such that a liquid medium flows. The culture under conditions such that a liquid medium flows is preferably culture under conditions such that a liquid medium flows to promote cell aggregation. Examples of the culture under conditions such that a liquid medium flows to promote cell aggregation include culture under conditions such that stresses (centrifugal force, centripetal force) due to a flow such as a rotational flow and a rocking flow force cells to gather at a point, and culture under conditions such that a liquid medium flows in linear reciprocating motion; particularly preferred is culture using a rotational flow and/or a rocking flow.

Vessels that cause less cell adhesion to the inner surface thereof are preferred as the culture vessel for the suspension culture. Examples of such vessels that cause less cell adhesion to the inner surface thereof include plates, the surface of which is hydrophilized by a biocompatible material. An applicable example thereof is, but not particularly limited to, a Nunclon™ Sphera (Thermo Fisher Scientific K.K.). The shape of the culture vessel is not particularly limited, and examples of the shape of the culture vessel include a dish, a flask, a well, a bag, and a spinner flask.

The period for aggregate formation is not particularly limited as long as the period exceeds 6 hours; specifically, aggregate formation is preferably performed for a period of 1 day, 2 days, 3 days, 4 days, 5 days, 6 days, 7 days, or 2 weeks, 3 weeks, 4 weeks, 5 weeks, 6 weeks, 7 weeks, or 8 weeks.

The medium for the suspension culture is not particularly limited as long as components which allow pluripotent stem cells to proliferate are contained in the medium, and applicable examples include a mTeSR1 (VERITAS Corporation) medium containing 1 to 100 µM of Y-27632 (Cayman Chemical) and an Essential 8™ containing 1 to 100 mg/mL of BSA.

The conditions for stirring or rotating in the suspension culture are not particularly limited as long as pluripotent stem cells can form an aggregate in a suspension, and the upper limit can be preferably 200 rpm, more preferably 150 rpm, even more preferably 120 rpm, more preferably 115 rpm, more preferably 110 rpm, more preferably 105 rpm, further preferably 100 rpm, more preferably 95 rpm, and particularly preferably 90 rpm. The lower limit can be preferably 1 rpm, more preferably 10 rpm, even more preferably 50 rpm, more preferably 60 rpm, more preferably 70 rpm, even more preferably 80 rpm, and further preferably 90 rpm. The rotation width in rotation culture is not particularly limited, and the lower limit can be, for example, 1 mm, preferably 10 mm, more preferably 20 mm, and the most preferably 25 mm. The upper limit of the rotation width can be, for example, 200 mm, preferably 100 mm, preferably 50 mm, more preferably 30 mm, and the most preferably 25 mm. Likewise, the rotation radius in rotation culture is not particularly limited, and preferably set so that the rotation width falls within the above range. The lower limit of the rotation radius can be, for example, 5 mm, and preferably 10 mm, and the upper limit can be, for example, 100 mm, and preferably 50 mm. Setting the conditions for rotation culture to satisfy these ranges is preferred because cell aggregates with appropriate dimensions can be readily produced.

The suspension culture may be based on rocking culture, in which a liquid medium is flowed through stirring by rocking. The rocking culture is performed by rocking a culture vessel containing a liquid medium and cells in a plane roughly perpendicular to the horizontal plane. The rocking speed is not particularly limited, and rocking can be performed with a frequency, for example, of 2 to 50 cycles, preferably of 4 to 25 cycles (one round is regarded as one cycle) per minute. The rocking angle is not particularly limited, and can be, for example, 0.1° to 20°, and more preferably 2° to 10°. Setting the conditions for rocking culture to satisfy these ranges is preferred because cell clumps with appropriate dimensions are successfully produced.

In addition, culture can be performed with stirring in motion as a combination of rotating and rocking as described above.

Suspension culture using a spinner flask culture vessel is a culture involving stirring a liquid medium by using a stirring blade in the culture vessel. The rotation frequency and amount of a medium are not particularly limited. In using a commercially available spinner flask culture vessel, the amount of culture solution recommended by the manufacturer can be suitably used, where a spinner flask from ABLE Corporation or the like can be suitably used, for example.

In the present invention, the seeding density for cells in the suspension culture is not particularly limited as long as the seeding density allows cells to form an aggregate; however, the seeding density is preferably $1 \times 10^5$ to $1 \times 10^7$ cells/mL. The seeding density for cells is preferably $2 \times 10^5$ cells/mL or more, $3 \times 10^5$ cells/mL or more, $4 \times 10^5$ cells/mL or more, or $5 \times 10^5$ cells/mL or more, and, preferably $9 \times 10^6$ cells/mL or less, $8 \times 10^6$ cells/mL or less, $7 \times 10^6$ cells/mL or less, $6 \times 10^6$ cells/mL or less, $5 \times 10^6$ cells/mL or less, $4 \times 10^6$ cells/mL or less, $3 \times 10^6$ cells/mL or less, $2 \times 10^6$ cells/mL or less, $1.9 \times 10^6$ cells/mL or less, $1.8 \times 10^6$ cells/mL or less, $1.7 \times 10^6$ cells/mL or less, $1.6 \times 10^6$ cells/mL or less, or $1.5 \times 10^6$ cells/mL or less. In particular, cell densities from $5 \times 10^5$ cells/mL to $1.5 \times 10^6$ cells/mL are suitable.

An aggregate of cells includes several hundreds to several thousands of cells. In the present invention, the size (diameter) of a cell aggregate is not particularly limited, and, for example, 50 μm or larger, 55 μm or larger, 60 μm or larger, 65 μm or larger, 70 μm or larger, 80 μm or larger, 90 μm or larger, 100 μm or larger, 110 μm or larger, 120 μm or larger, 130 μm or larger, 140 μm or larger, or 150 μm or larger, and, 1000 μm or smaller, 900 μm or smaller, 800 μm or smaller, 700 μm or smaller, 600 μm or smaller, 500 μm or smaller, or 400 μm or smaller. Cell aggregates of 150 μm to 400 μm in diameter are suitable for the present invention. A cell aggregate having a diameter out of the above range may coexist.

The amount of culture solution in the suspension culture can be appropriately adjusted in accordance with a culture vessel therefor, and in using a 12-well plate (the bottom surface area of a well in a planar view is 3.5 cm$^2$), for example, the amount of culture solution can be 0.5 mL/well or more and 1.5 mL/well or less, and more preferably 1 mL/well. In using a 6-well plate (the bottom surface area of a well in a planar view is 9.6 cm$^2$), for example, the amount of culture solution can be 1.5 mL/well or more, preferably 2 mL/well or more, more preferably 3 mL/well or more, and, 6.0 mL/well or less, preferably 5 mL/well or less, more preferably 4 mL/well or less. In using a 125 mL-Erlenmeyer flask (an Erlenmeyer flask having a capacity of 125 mL), for example, the amount of culture solution can be 10 mL/vessel or more, preferably 15 mL/vessel or more, more preferably 20 mL/vessel or more, more preferably 25 mL/vessel or more, more preferably 20 mL/vessel or more, more preferably 25 mL/vessel or more, more preferably 30 mL/vessel or more, and, 50 mL/vessel or less, more preferably 45 mL/vessel or less, more preferably 40 mL/vessel or less. In using a 500 mL-Erlenmeyer flask (an Erlenmeyer flask having a capacity of 500 mL), for example, the amount of culture solution can be 100 mL/vessel or more, preferably 105 mL/vessel or more, more preferably 110 mL/vessel or more, more preferably 115 mL/vessel or more, more preferably 120 mL/vessel or more, and, 150 mL/vessel or less, more preferably 145 mL/vessel or less, more preferably 140 mL/vessel or less, more preferably 135 mL/vessel or less, more preferably 130 mL/vessel or less, more preferably 125 mL/vessel or less. In using a 1000 mL-Erlenmeyer flask (an Erlenmeyer flask having a capacity of 1000 mL), for example, the amount of culture solution can be 250 mL/vessel or more, preferably 260 mL/vessel or more, more preferably 270 mL/vessel or more, more preferably 280 mL/vessel or more, more preferably 290 mL/vessel or more, and, 350 mL/vessel or less, more preferably 340 mL/vessel or less, more preferably 330 mL/vessel or less, more preferably 320 mL/vessel or less, more preferably 310 mL/vessel or less. In using a 2000 mL-Erlenmeyer flask (an Erlenmeyer flask having a capacity of 2000 mL), for example, the amount of culture solution can be 500 mL/vessel or more, more preferably 550 mL/vessel or more, more preferably 600 mL/vessel or more, and, 1000 mL/vessel or less, more preferably 900 mL/vessel or less, more preferably 800 mL/vessel or less, more preferably 700 mL/vessel or less. In using a 3000 mL-Erlenmeyer flask (an Erlenmeyer flask having a capacity of 3000 mL), for example, the amount of culture solution can be 1000 mL/vessel or more, preferably 1100 mL/vessel or more, more preferably 1200 mL/vessel or more, more preferably 1300 mL/vessel or more, more preferably 1400 mL/vessel or more, more preferably 1500 mL/vessel or more, and, 2000 mL/vessel or less, more preferably 1900 mL/vessel or less, more preferably 1800 mL/vessel or less, more preferably 1700 mL/vessel or less, more preferably 1600 mL/vessel or less. In using a 2 L-culture bag (a disposable culture bag having a capacity of 2 L), for example, the amount of culture solution can be 100 mL/bag or more, more preferably 200 mL/bag or more, more preferably 300 mL/bag or more, more preferably 400 mL/bag or more, more preferably 500 mL/bag or more, more preferably 600 mL/bag or more, more preferably 700 mL/bag or more, more preferably 800 mL/bag or more, more preferably 900 mL/bag or more, more preferably 1000 mL/bag or more, and, 2000 mL/bag or less, more preferably 1900 mL/bag or less, more preferably 1800 mL/bag or less, more preferably 1700 mL/bag or less, more preferably 1600 mL/bag or less, more preferably 1500 mL/bag or less, more preferably 1400 mL/bag or less, more preferably 1300 mL/bag or less, more preferably 1200 mL/bag or less, more preferably 1100 mL/bag or less. In using a 10 L-culture bag (a disposable culture bag having a capacity of 10 L), for example, the amount of culture solution can be 500 mL/bag or more, more preferably 1 L/bag or more, more preferably 2 L/bag or more, more preferably 3 L/bag or more, more preferably 4 L/bag or more, more preferably 5 L/bag or more, and, 10 L/bag or less, more preferably 9 L/bag or less, more preferably 8 L/bag or less, more preferably 7 L/bag or less, more preferably 6 L/bag or less. In using a 20 L-culture bag (a disposable culture bag having a capacity of 20 L), for example, the amount of culture solution can be 1 L/bag or more, more preferably 2 L/bag or more, more preferably 3 L/bag or more, more preferably 4 L/bag or more, more preferably 5 L/bag or more, more preferably 6 L/bag or more, more preferably 7 L/bag or more, more preferably 8 L/bag or more, more preferably 9 L/bag or more, more preferably 10 L/bag or more, and, 20 L/bag or less, more preferably 19 L/bag or less, more preferably 18 L/bag or less, more preferably 17 L/bag or less, more preferably 16 L/bag or less, more preferably 15 L/bag or less, more preferably 14 L/bag or less, more preferably 13 L/bag or less, more preferably 12 L/bag or less, more preferably 11 L/bag or less. In using a 50 L-culture bag (a disposable culture bag having a capacity of 50 L), for example, the amount of culture solution can be 1 L/bag or more, more preferably 2 L/bag or more, more preferably 5 L/bag or more, more preferably 10 L/bag or more, more preferably 15 L/bag or more, more preferably 20 L/bag or more, more preferably 25 L/bag or more, and, 50 L/bag or less, more preferably 45 L/bag or less, more preferably 40 L/bag or less, more preferably 35 L/bag or less, more preferably 30 L/bag or less. With the amount of culture solution falling within the range, cell aggregates of appropriate size are likely to form.

The capacity of the culture vessel for use is not particularly limited and can be appropriately selected, and applicable is a culture vessel such that the lower limit of the area of a bottom surface of a portion to contain a liquid medium in a planar view is, for example, 0.32 cm$^2$, preferably 0.65 cm$^2$, more preferably 0.65 cm$^2$, even more preferably 1.9 cm$^2$, further preferably 3.0 cm$^2$, 3.5 cm$^2$, 9.0 cm$^2$, or 9.6 cm$^2$, and the upper limit is, for example, 1000 cm$^2$, preferably 500 cm$^2$, more preferably 300 cm$^2$, more preferably 150 cm$^2$, more preferably 75 cm$^2$, further preferably 55 cm$^2$, even more preferably 25 cm$^2$, even more preferably 21 cm$^2$, furthermore preferably 9.6 cm$^2$, or 3.5 cm$^2$.

The culture temperature is not particularly limited as long as the culture temperature is suitable for culture of pluripotent stem cells for use, and typically 30° C. to 40° C., and preferably approximately 37° C.

It is preferred to culture under an atmosphere with a $CO_2$ concentration of about 1 to 10%, preferably of 5%, by using a $CO_2$ incubator or the like.

[5] Preculture of Pluripotent Stem Cells

Before allowed to be induced to differentiate into a cell population of any of three germ layers, the aggregates of pluripotent stem cells or pluripotent stem cells are subjected to suspension culture using a medium containing 2-mercaptoethanol to prepare a cell population.

In accordance with the type of cells, an MEM medium, a BME medium, a DMEM medium, a DMEM/F12 medium, an αMEM medium, an IMDM medium, an ES medium, a DM-160 medium, a Fisher medium, an F12 medium, a WE medium, an RPMI1640 medium, an Essential 6™ medium (Thermo Fisher Scientific K.K.) or the like can be used as a medium for the preculture.

The preculture of pluripotent stem cells is performed on the basis of suspension culture. The preculture can be performed under the above-described conditions for suspension culture, and in addition cells may be adhered to a microcarrier or the like in advance before suspension culture, cell clumps composed only of cells may be subjected to suspension culture, and a polymer such as collagen may coexist in cell clumps; thus, the form of the preculture is not particularly limited.

The concentration of 2-mercaptoethanol in the medium for the preculture is not particularly limited as long as the concentration is within a range that enhances the efficiency of differentiation induction, and, for example, the concentration of 2-mercaptoethanol is preferably 1 μM or more, 2 μM or more, 5 μM or more, 10 μM or more, 20 μM or more, 30 μM or more, 40 μM or more, or 50 μM or more, and preferably 200 μM or less, 150 μM or less, 120 μM or less, 100 μM or less, 90 μM or less, 80 μM or less, 70 μM or less, or 60 μM or less.

It is also preferable that the medium for the preculture be a medium to which FGF2 (Fibroblast Growth Factor 2) is not added. It has been revealed in the present invention that use of a medium to which FGF2 is not added can more enhance the differentiation efficiency of a cell population into any of three germ layers.

It is also preferable that the medium for the preculture be a medium to which TGFβ1 (Transforming growth factor-β1) is not added. It has been revealed in the present invention that use of a medium to which TGFβ1 is not added can more enhance the differentiation efficiency of a cell population into any of three germ layers.

It is also preferable that the medium for the preculture be a medium to which a WNT signaling activator is not added. It has been revealed in the present invention that use of a medium to which a WNT signaling activator is not added can more enhance the differentiation efficiency of a cell population into any of three germ layers.

It is also preferable that the medium for the preculture be a medium to which activin A (herein, "ACTIVIN A" is occasionally used synonymously) is not added. It has been revealed in the present invention that use of a medium to which activin A is not added can more enhance the differentiation efficiency of a cell population into any of three germ layers.

It is also preferable that the medium for the preculture be a medium further containing insulin. It has been revealed in the present invention that use of a medium containing insulin can more enhance the differentiation efficiency of a cell population into any of three germ layers.

Amino acids, antibiotics, antioxidants, and other additives may be added to the medium for the preculture. For example, 0.1 to 2% (volume/volume) of non-essential amino acids, 0.1 to 2% (volume/volume) of penicillin/streptomycin, 0.1 to 20 mg/mL of BSA or 1 to 20% (volume/volume) of Knockout serum replacement (KSR), and so forth may be added.

The culture temperature is not particularly limited as long as the culture temperature is suitable for culture of pluripotent stem cells for use, and typically 30° C. to 40° C., and preferably approximately 37° C.

It is preferred to culture under an atmosphere with a $CO_2$ concentration of about 1 to 10%, preferably of 5%, by using a $CO_2$ incubator or the like.

The culture period for the preculture of pluripotent stem cells is not particularly limited as long as the culture period is days that allow culturing until enhanced pluripotency is achieved; for example, a period that does not exceed 1 week can be employed. More specifically, the culture period is shorter than 6 days, shorter than 5 days, shorter than 4 days, shorter than 3 days, or 6 hours to 48 hours, about 12 hours to 36 hours, or 18 hours to 24 hours.

[6] Differentiation Induction Into Cell Population of Any of Three Germ Layers

In the present invention, the cell population obtained by the above-described preculture is cultured under conditions that allow the cell population to be induced to differentiate into any of an endodermal cell, a mesodermal cell, or an ectodermal cell, thereby producing a cell population of any of three germ layers.

In allowing pluripotent stem cells to be induced to differentiate into a cell population of any of three germ layers, the pluripotent stem cells are cultured by using a differentiation-inducing medium.

The differentiation-inducing medium is not particularly limited as long as the differentiation-inducing medium is a medium that allows pluripotent stem cells to be induced to differentiate, and examples thereof include a serum-containing medium and a serum-free medium containing serum replacement components.

Any of a medium for primate ES/iPS cells (ReproCELL medium), a BME medium, a BGJb medium, a CMRL 1066 medium, a Glasgow MEM medium, an Improved MEM Zinc Option medium, an IMDM medium, a Medium 199 medium, an Eagle MEM medium, an αMEM medium, a DMEM medium, a Ham's medium, an RPMI1640 medium, a Fischer's medium, and a mixed medium of two or more media arbitrarily selected from these media can be used in accordance with the type of cells. The medium is not particularly limited as long as the medium is a medium applicable to culturing animal cells.

The differentiation induction medium may contain a serum component or serum replacement component. Examples of the serum component or serum replacement component include albumin, insulin, transferrin, fatty acids, collagen precursors, trace elements (e.g., zinc, selenium), B-27 Supplement (Thermo Fisher Scientific K.K.), N2 Supplement, N21 Supplement (R&D Systems, Inc.), the supplement NeuroBrew-21 (Miltenyi Biotec), KSR 2-mercaptoethanol, and 3'thiolglycerol, and equivalents to them.

Various additives, antibiotics, antioxidants, and so forth may be added to the differentiation induction medium. For example, 0.1 mM to 5 mM of sodium pyruvate, 0.1 to 2% (volume/volume) of non-essential amino acids, 0.1 to 2% (volume/volume) of penicillin, 0.1 to 2% (volume/volume) of streptomycin, and 0.1 to 2% (volume/volume) of amphotericin B, catalase, glutathione, galactose, retinoic acid (vitamin A), superoxide dismutase, ascorbic acid (vitamin C), D-α-tocopherol (vitamin E), and so forth may be added.

A differentiation induction factor is further added to the differentiation induction medium. Details of the differentiation induction factor will be described later.

The culture of pluripotent stem cells in differentiation induction is preferably based on suspension culture. Cells may adhere to a microcarrier or the like in advance before suspension culture, cell clumps composed only of cells may be subjected to suspension culture, and a polymer such as collagen may coexist in cell clumps; thus, the form of the culture is not particularly limited.

The culture temperature in culturing for differentiation induction is not particularly limited as long as the culture temperature is suitable for culture of pluripotent stem cells for use, and typically 30° C. to 40° C., and preferably approximately 37° C.

It is preferred to culture under an atmosphere with a $CO_2$ concentration of about 1 to 10%, preferably of 5%, by using a $CO_2$ incubator or the like.

The culture period for the culture for differentiation from pluripotent stem cells into endodermal cells is not particularly limited as long as a cell type that exhibits endodermal cell properties is achieved; for example, a culture period within 2 weeks can be employed, and, more specifically, the culture period is 2 days or longer and 8 days or shorter, more preferably 2 days or longer and 7 days or shorter, and even more preferably 3 days or longer and 6 days or shorter, and an example is 5 days.

[7] Differentiation Induction Factor and Other Additives for Differentiation Induction into Endodermal Cells In the production method of the present invention for an endodermal cell, pluripotent stem cells are cultured in a medium containing a TGFβ (Transforming growth factor-β) superfamily signaling activator, and then cultured in a medium to which FGF2 and BMP4 (Bone morphogenetic protein 4) are not added.

The TGFβ superfamily signaling plays key roles in regulation of cell proliferation, differentiation, and development in a wide variety of biological systems. In general, signaling is initiated by multimer formation of serine/threonine receptor kinase caused by the ligand, and phosphorylation of an intracellular signaling molecule such as Smad1/5/8 for the bone morphogenetic protein (BMP) pathway, or phosphorylation of Smad2/3 for the TGFβ/activin pathway and the NODAL/activin pathway. Phosphorylation of the carboxyl group terminal of Smads by an activated receptor results in partner formation with Smad4, a signal transducer of the same family, to promote nuclear translocation. It is known that activated Smads control various biological effects through partnering with a transcription factor to perform cell-state-specific transcriptional regulation.

Examples of genes involved in the TGFβ superfamily signaling pathway include a BMP2 gene, a BMP4 gene, a BMP5 gene, a BMP6 gene, a BMP7 gene, a BMP8 gene, a GDF5 (Growth differentiation factor 5) gene, a GDF6 gene, a GDF7 gene, a GDF8 gene, an AMH (anti-Mullerian hormone) gene, a paired-like homeodomain 2 (PITX2) gene, and a NODAL gene.

The TGFβ superfamily signaling activator is not particularly limited as long as the TGFβ superfamily signaling activator is a substance that activates signaling for the bone morphogenetic protein (BMP) pathway, the TGFβ/activin pathway, and/or the NODAL/activin pathway; for example, activin A, FGF2, BMP4, BMP5, BMP6, BMP7, BMP8, GDF5, GDF6, GDF7, GDF8, AMH, PITX2, and/or NODAL can be used. In particular, a substance that activates signaling for the TGFβ/activin pathway can be suitably used; specifically use of at least one selected from the group consisting of activin A, FGF2, and BMP4 is preferred, and use of all of activin A, FGF2, and BMP4 is particularly preferred.

When activin A is used for the medium containing a TGFβ superfamily signaling activator, the initial concentration of activin A added is preferably 1 ng/mL or more, 2 ng/mL or more, 3 ng/mL or more, 5 ng/mL or more, 10 ng/mL or more, 20 ng/mL or more, 30 ng/mL or more, 40 ng/mL or more, or 50 ng/mL or more, and, preferably 1,000 ng/mL or less, 900 ng/mL or less, 800 ng/mL or less, 700 ng/mL or less, 600 ng/mL or less, 500 ng/mL or less, 400 ng/mL or less, 300 ng/mL or less, 200 ng/mL or less, 150 ng/mL or less, or 100 ng/mL or less.

When FGF2 is used for the medium containing a TGFβ superfamily signaling activator, the initial concentration of FGF2 added is preferably 1 ng/mL or more, 2 ng/mL or more, 3 ng/mL or more, 5 ng/mL or more, 10 ng/mL or more, 20 ng/mL or more, 30 ng/mL or more, or 40 ng/mL or more, and, preferably 1,000 ng/mL or less, 900 ng/mL or less, 800 ng/mL or less, 700 ng/mL or less, 600 ng/mL or less, 500 ng/mL or less, 400 ng/mL or less, 300 ng/mL or less, 200 ng/mL or less, 150 ng/mL, 100 ng/mL or less, 90 ng/mL or less, 80 ng/mL or less, or 70 ng/mL or less.

When BMP4 is used for the medium containing a TGFβ superfamily signaling activator, the initial concentration of BMP4 added is preferably 1 ng/mL or more, 2 ng/mL or more, 3 ng/mL or more, 5 ng/mL or more, 6 ng/mL or more, 7 ng/mL or more, 8 ng/mL or more, 9 ng/mL or more, 10 ng/mL or more, 11 ng/mL or more, 12 ng/mL or more, 13 ng/mL or more, 14 ng/mL or more, or 15 ng/mL or more, and, preferably 1,000 ng/mL or less, 900 ng/mL or less, 800 ng/mL or less, 700 ng/mL or less, 600 ng/mL or less, 500 ng/mL or less, 400 ng/mL or less, 300 ng/mL or less, 200 ng/mL or less, 150 ng/mL, 100 ng/mL or less, 90 ng/mL or less, 80 ng/mL or less, 70 ng/mL or less, 60 ng/mL or less, 50 ng/mL or less, 40 ng/mL or less, or 30 ng/mL or less.

The medium to which FGF2 and BMP4 are not added preferably contains activin A.

When the medium to which FGF2 and BMP4 are not added contains activin A, the initial concentration of activin A added is preferably 1 ng/mL or more, 2 ng/mL or more, 3 ng/mL or more, 5 ng/mL or more, 10 ng/mL or more, 20 ng/mL or more, 30 ng/mL or more, 40 ng/mL or more, or 50 ng/mL or more, and, preferably 1,000 ng/mL or less, 900 ng/mL or less, 800 ng/mL or less, 700 ng/mL or less, 600 ng/mL or less, 500 ng/mL or less, 400 ng/mL or less, 300 ng/mL or less, 200 ng/mL or less, 150 ng/mL or less, or 100 ng/mL or less.

The medium to which FGF2 and BMP4 are not added preferably contains at least one or more selected from the group consisting of insulin, transferrin, sodium selenite, and ethanolamine.

The concentration of insulin added is preferably 0.001 µg/mL or more, 0.01 µg/mL or more, 0.05 µg/mL or more, 0.1 µg/mL or more, or 0.2 µg/mL or more, and, preferably 10,000 µg/mL or less, 1,000 µg/mL or less, 100 µg/mL or less, 10 µg/mL or less, 9 µg/mL or less, 8 µg/mL or less, 7 µg/mL or less, 6 µg/mL or less, 5 µg/mL or less, 4 µg/mL or less, 3 µg/mL or less, or 2 µg/mL or less. The concentration of transferrin added is preferably 0.001 µg/mL or more, 0.01 µg/mL or more, 0.05 µg/mL or more, 0.06 µg/mL or more, 0.07 µg/mL or more, 0.08 µg/mL or more, 0.09 µg/mL or more, 0.1 µg/mL or more, or 0.11 µg/mL or more, and, preferably 10,000 µg/mL or less, 1,000 µg/mL or less, 100 µg/mL or less, 10 µg/mL or less, 9 µg/mL or less, 8 µg/mL or less, 7 µg/mL or less, 6 µg/mL or less, 5 µg/mL or less, 4 µg/mL or less, 3 µg/mL or less, 2 µg/mL or less, 1.9 µg/mL or less, 1.8 µg/mL or less, 1.7 µg/mL or less, 1.6 µg/mL or less, 1.5 µg/mL or less, 1.4 µg/mL or less, 1.3 µg/mL or less, 1.2 µg/mL or less, or 1.1 µg/mL or less. The concentration of sodium selenite added is preferably 0.001 ng/mL or more, 0.01 ng/mL or more, or 0.1 ng/mL or more, and, preferably 10,000 ng/mL or less, 1,000 ng/mL or less, 100 ng/mL or less, 10 ng/mL or less, or 1 ng/mL or less. The concentration of ethanolamine added is preferably 0.001 µg/mL or more, 0.01 µg/mL or more, 0.02 µg/mL or more, 0.03 µg/mL or more, or 0.04 µg/mL or more, and, preferably 10,000 µg/mL or less, 1,000 µg/mL or less, 100 µg/mL or less, 10 µg/mL or less, 1 µg/mL or less, 0.9 µg/mL or less, 0.8 µg/mL or less, 0.7 µg/mL or less, 0.6 µg/mL or less, 0.5 µg/mL or less, or 0.4 µg/mL or less.

The medium containing a TGFβ superfamily signaling activator and/or medium to which FGF2 and BMP4 are not added preferably further contain(s) 2-mercaptoethanol. The action of 2-mercaptoethanol can enhance the differentiation induction efficiency into endodermal cells.

Preferably, the medium containing a TGFβ superfamily signaling activator further contains a WNT signaling activator.

WNT signaling is a series of actions to promote nuclear translocation of β-catenin to allow it to function as a transcription factor. The WNT signaling is due to intercellular interaction, and includes a series of processes that WNT3A as a protein secreted from a certain cell acts on another cell, and β-catenin in the cell undergoes nuclear translocation to act as a transcription factor. The series of processes causes the first phenomenon of organ construction, such as epithelial-mesenchymal interaction. The WNT signaling is known to control various cell functions including proliferation and differentiation of cells, and cell movement in organogenesis and early development through activation of three pathways, namely, the β-catenin pathway, PCP pathway, and Ca$^{2+}$ pathway.

Examples of genes involved in the WNT signaling pathway include a WNT3A gene.

The WNT signaling activator is not particularly limited, and may be any WNT signaling activator that exhibits inhibitory activity for glycogen synthase kinase-3 (GSK-3), and applicable are, for example, a bis-indolo (indirubin) compound (BIO) ((2'Z,3'E)-6-bromoindirubin-3'-oxime) and an acetoxime analogue thereof, namely, BIO-acetoxime (2'Z,3'E)-6-bromoindirubin-3'-acetoxime), a thiadiazolidine (TDZD) analogue (4-benzyl-2-methyl-1,2,4-thiadiazolidine-3,5-dione), an oxothiadiazolidine-3-thione analogue (2,4-dibenzyl-5-oxothiadiazolidine-3-thione), a thienyl α-chloromethyl ketone compound (2-chloro-1-(4,4-dibromo-thiophen-2-yl)-ethanone), a phenyl α bromomethyl ketone compound (α-4-dibromoacetophenone), a thiazole-containing urea compound (N-(4-methoxybenzyl)-N'-(5-nitro-1,3-thiazol-2-yl)urea), and a GSK-3β peptide inhibitor such as H-KEAPPAPPQSpP-NH2; CHIR99021 (CAS: 252917-06-9) can be particularly preferably used. In addition, WNT3A can be suitably used.

When CHIR99021 is used for the medium containing a TGFβ superfamily signaling activator, the initial concentration of CHIR99021 added is preferably 0.01 µM or more, 0.02 µM or more, 0.03 µM or more, 0.04 µM or more, 0.05 µM or more, 0.1 µM or more, 0.2 µM or more, 0.3 µM or more, 0.4 µM or more, 0.5 µM or more, 0.6 µM or more, 0.7 µM or more, 0.8 µM or more, 0.9 µM or more, 1 µM or more, or 2 µM or more, and, preferably 100 µM or less, 90 µM or less, 80 µM or less, 70 µM or less, 60 µM or less, 50 µM or less, 45 µM or less, 40 µM or less, 35 µM or less, 30 µM or less, 25 µM or less, 20 µM or less, 15 µM or less, 10 µM or less, or 5 µM or less. The initial concentration of CHIR99021 added is more preferably 3 µM or 4 µM.

The medium containing a TGFβ superfamily signaling activator and/or medium to which FGF2 and BMP4 are not added at least contain(s) glucose. The lower limit of the concentration of glucose contained in the medium is not particularly limited as long as the concentration allows cells to proliferate, but preferably 0.01 g/L or more. The upper limit of the concentration of glucose contained in the medium is not particularly limited as long as the concentration does not cause cell death, but preferably 10 g/L or less, for example. As another embodiment, a medium containing glucose in a concentration of less than 2.0 g/L is preferred from the viewpoint of efficient differentiation into endodermal somatic cells. The glucose concentration of the medium containing a TGFβ superfamily signaling activator and/or medium to which FGF2 and BMP4 are not added may be 1.0 g/L or less, 0.9 g/L or less, 0.8 g/L or less, 0.7 g/L or less, or 0.6 g/L or less. The lower limit of the glucose concentration when the medium containing a TGFβ superfamily signaling activator and/or medium to which FGF2 and BMP4 are not added contain(s) glucose is not particularly limited, and may be 0.01 g/L or more, 0.02 g/L or more, 0.05 g/L or more, 0.1 g/L or more, 0.2 g/L or more, 0.3 g/L or more, 0.4 g/L or more, or 0.5 g/L or more.

Use of a medium containing glucose in a concentration of 1.0 g/L or less as the medium containing a TGFβ superfamily signaling activator and/or medium to which FGF2 and BMP4 are not added decreases the number of SOX2-positive cells and increases the number of SOX17-positive cells, and hence a cell population more suitable for differentiation induction into somatic cells can be obtained.

[8] Endodermal Cell Population

The present invention provides an endodermal cell population, wherein a relative expression level of a Nanog gene to an expression level of an OAZ1 gene is 0.8 or less, a relative expression level of an HNF1B gene to an expression level of the OAZ1 gene is 1.0 or more, and a proportion of SOX17-positive cells is 80% or more.

The relative expression level of a Nanog (Nanog homeobox, refer to ID: 79923 registered in a gene database from National Center for Biotechnology Information for the gene sequence) gene to the expression level of OAZ1 (ornithine decarboxylase antizyme 1, refer to ID: 4946 registered in a gene database from National Center for Biotechnology Information for the gene sequence) gene is 0.8 or less, but may be preferably 0.7 or less, 0.65 or less, 0.6 or less, 0.55 or less, 0.5 or less, 0.45 or less, 0.4 or less, or 0.35 or less. Since Nanog is an undifferentiation marker, the situation that the relative expression level of the Nanog gene to the expression level of the OAZ1 gene is 0.8 or less indicates a low degree of undifferentiation, that is, a reduced number of undifferentiated cells in a cell population, which is an indication of ongoing efficient differentiation induction.

The relative expression level of HNF1B (hepatocyte nuclear factor 1 beta, the gene sequence thereof is referred to ID: 6928 registered in the gene database of National Center for Biotechnology Information) to the expression level of the OAZ1 gene is 1.0 or more. Preferably, it may be 1.1 or more, 1.2 or more, 1.5 or more, 1.7 or more, 2.0 or more, 2.3 or more, or 2.5 or more. HNF1B is a primitive gut tube (PGT) cell marker. Thus, the fact that the relative expression level of the HNF1B gene to the expression level of the OAZ1 gene is 1.0 or more means that the cell population is more suitable for differentiation induction into somatic cells of endodermal lineage.

In the endodermal cell population of the present invention, the proportion of SOX17 (sex determining region Y-box 17)-positive cells is 80% or more. Preferably, it may be 85% or more, 90% and more, 91% or more, 92% or more, 93% or more, 94% or more, 95% or more, 96% or more, 97% or more, 98% or more, or 99% or more, 99.5 or more or 99.9 or more. SOX17 is an endodermal marker. Thus, the fact that the proportion of SOX17-positive is 80% or more means that differentiation induction to definitive endoderm (DE) is efficiently performed. For measuring the proportion of SOX17-positive cells, anti-SOX17 antibody (catalog number: 562594) manufactured by Becton, Dickinson and Company may be preferably used.

Preferably, the relative expression level of HNF4A (hepatocyte nuclear factor 4 alpha, the gene sequence thereof is referred to ID: 3172 registered in the gene database of National Center for Biotechnology Information) to the expression level of the OAZ1 gene is 0.5 or more. Preferably, it may be 0.6 or more, 0.65 or more, 0.7 or more, 0.75 or more, 1.0 or more, 1.5 or more, 2.0 or more, 2.3 or more, or 3 or more. HNF4A is a primitive gut cell (PGT) marker. Thus, the fact that the relative expression level of the HNF4A gene to the expression level of the OAZ1 gene is 0.5 or more means that the cell population is more suitable for differentiation induction into somatic cells of an endodermal lineage.

Preferably, the relative expression level of EpCAM (epithelial cell adhesion molecule, the gene sequence thereof is referred to ID: 4072 registered in the gene database of National Center for Biotechnology Information) to the expression level of the OAZ1 gene is 0.6 or more. Preferably, it may be 0.7 or more, 0.8 or more, 0.9 or more, 1.0 or more, 1.1 or more, 1.2 or more, 1.3 or more, 1.5 or more, or 2.0 or more. EpCAM is an endodermal marker. Thus, the fact that the relative expression level of the EpCAM gene to the expression level of the OAZ1 gene is 0.6 or more means that the cell population is more suitable for differentiation induction into somatic cells of an endodermal lineage.

Preferably, the relative expression level of VIM (vimentin, the gene sequence thereof is referred to ID: 7431 registered in the gene database of National Center for Biotechnology Information) to the expression level of the OAZ1 gene is 12 or less. More preferably, it may be 11 or less, 10 or less, 9 or less, 8 or less, 7 or less, 6 or less, 5 or less, 4 or less, 3.5 or less, or 3.0 or less. VIM is a mesenchymal marker. Thus, the fact that the relative expression level of the VIM gene to the expression level of the OAZ1 gene is 12 or less means that the cell population is more suitable for differentiation induction into somatic cells of an endodermal lineage.

Preferably, the relative expression level of SOX2 (sex determining regulation Y-box 2, the gene sequence thereof is referred to ID: 6657 registered in the gene database of National Center for Biotechnology Information) to the expression level of the OAZ1 gene is 0.11 or less. More preferably, it may be 0.10 or less, 0.07 or less, 0.05 or less, 0.01 or less, 0.006 or less, or 0.0045 or less. SOX2 is an undifferentiated marker. Thus, the fact that the relative expression level of the SOX2 gene to the expression level of the OAZ1 gene is 0.11 or less means effective induction of differentiation because of indicating a lower degree of differentiation, i.e., a decrease in a number of undifferentiated cells in the cell population.

Preferably, the relative expression level of c-Myc (v-myc avian myelocytomatosis viral oncogene homolog, the gene sequence thereof is referred to ID: 4609 registered in the gene database of National Center for Biotechnology Information) to the expression level of the OAZ1 gene is 0.1 or less. More preferably, it may be 0.095 or less, 0.05 or less, 0.045 or less, 0.035 or less, 0.02 or less, 0.015 or less, or 0.01 or less. c-Myc is an undifferentiated marker. Thus, the fact that the relative expression level of the cMyc gene to the expression level of the OAZ1 gene is 0.1 or less means effective induction of differentiation because of indicating a lower degree of differentiation, i.e., a decrease in a number of undifferentiated cells in the cell population.

Preferably, the relative expression level of OCT4 (octamer-binding transcription factor 4, the gene sequence thereof is referred to ID: 5460 registered in the gene database of National Center for Biotechnology Information) to the expression level of the OAZ1 gene is 0.4 or less. More preferably, it may be 0.35 or less, 0.3 or less, 0.25 or less, 0.2 or less, 0.15 or less, 0.1 or less, 0.05 or less or 0.01 or less. OCT4 is an undifferentiated marker. Thus, the fact that the relative expression level of the OCT4 gene to the expression level of the OAZ1 gene is 0.4 or less means effective induction of differentiation because of indicating a lower degree of differentiation, i.e., a decrease in a number of undifferentiated cells in the cell population.

Preferably, the relative expression level of Fibronectin-1 (Fibronectin-1, the gene sequence thereof is referred to ID: 2335 registered in the gene database of National Center for Biotechnology Information) to the expression level of the OAZ1 gene is 1.0 or more. Preferably, it may be 1.1 or more, 1.2 or more, 1.3 or more, 1.4 or more, 1.5 or more, or 1.6 or more. Fibronectin-1 is a molecule involved in ECM (extracellular matrix) receptor interaction. It is known that ECM not only serves as a scaffold for cells, but also works to produce signals required for tissue morphogenesis, differentiation, and homeostasis. Thus, the fact that the relative expression level of Fibronectin-1 to the expression level of the OAZ1 gene is 1.0 or more means that the cell population is more suitable for differentiation induction into somatic cells of an endodermal lineage.

Preferably, the relative expression level of Cyclin D1 (Cyclin D1, the gene sequence thereof is referred to ID: 595 registered in the gene database of National Center for Biotechnology Information) to the expression level of the OAZ1 gene is 0.015 or less. More preferably, it may be 0.014 or less, 0.013 or less, 0.012 or less, or 0.011 or less. Cyclin D1 is involved in the cell cycle. Thus, the fact that the relative expression level of the Cyclin D1 gene to the expression level of the OAZ1 gene is 0.015 or less indicates that the cell cycle is likely to be arrested (a state in which cell proliferation is suppressed). Therefore, it means that more efficient differentiation induction is performed.

Preferably, the relative expression level of Matrix metallopeptidase 2 (Matrix metallopeptidase 2, the gene sequence thereof is referred to ID: 4313 registered in the gene database of National Center for Biotechnology Information) to the expression level of the OAZ1 gene is 0.020 or less. More preferably, it may be 0.019 or less, 0.018 or less, or 0.017 or less. Matrix metallopeptidase 2 is known to be involved in angiogenesis and the like in cancer and also known to degrade extracellular matrix, such as collagen, which makes up the basement membrane. Thus, the fact that the relative expression level of the Matrix metallopeptidase 2 gene to the expression level of the OAZ1 gene is 0.020 or less indicates that suppressed degradation of the extracellular matrix, stabilized contact with the ECM, such as Fibronectin-1, facilitated entry of signals required for morphogenesis, differentiation, and homeostasis of the tissue can be attained. Therefore, it means that more efficient differentiation induction is performed.

Preferably, the relative expression level of CD44 (CD44, the gene sequence thereof is referred to ID: 960 registered in the gene database of National Center for Biotechnology Information) to the expression level of the OAZ1 gene is 0.020 or less. More preferably, it may be 0.019 or less, 0.018 or less, 0.017 or less, or 0.016 or less, 0.015 or less, 0.014 or less, 0.013 or less, 0.012 or less, 0.011 or less, 0.010 less, or 0.009 or less. CD44 is known as an adhesion molecule having hyaluronic acid as the main ligand and also known to be involved in the proliferation ability and the like of cancer cells. Thus, the fact that the relative expression level of the CD44 gene to the expression level of the OAZ1 gene is 0.020 or less indicates that cell growth is suppressed. Therefore, it means that more efficient differentiation induction is performed.

Preferably, the relative expression level of insulin receptor substrate 1 (insulin receptor substrate 1, the gene sequence thereof is referred to ID: 3667 registered in the gene database of National Center for Biotechnology Information) to the expression level of the OAZ1 gene is 0.0010 or less. More preferably, it may be 0.0009 or less, 0.0008 or less, or 0.0007 or less. Insulin receptor substrate 1 is a molecule involved in PI3K (phosphatidylinositol 3-kinase)-Akt signaling pathway. It is known that differentiation is suppressed when the PI3K-Akt signal is activated. Thus, the fact that the relative expression level of the insulin receptor substrate 1 gene to the expression level of the OAZ1 gene is 0.0010 or less indicates that the PI3K-Akt signal is hardly entered. Therefore, it means that more efficient differentiation induction is performed.

The relative expression level of the Nanog gene to the expression level of the OAZ1 gene, the relative expression level of the HNF1B gene relative to the expression level of the OAZ1 gene, the relative expression level of the HNF4A gene to the expression level of the OAZ1 gene, the relative expression level of the EpCAM gene to the expression level of the OAZ1 gene, the relative expression level of the VIM gene to the expression level of the OAZ1 gene, the relative expression level of the SOX2 gene to the expression level of the OAZ1 gene, the relative expression level of the OCT4 gene to the expression level of the OAZ1 gene, the relative expression level of the c-Myc gene to the expression level of the OAZ1 gene, the relative expression level of the Fibronectin-1 gene to the expression level of the OAZ1 gene, the relative expression level of the Cyclin D1 gene to the expression level of the OAZ1 gene, the relative expression level of the Matrix metallopeptidase 2 gene to the expression level of the OAZ1 gene, the relative expression level of the CD44 gene to the expression level of the OAZ1 gene, and the relative expression level of the insulin receptor substrate 1 gene to the expression level of the OAZ1 gene mean the proportions of the expression levels of the Nanog gene, HNF1B gene, HNF4A gene, EpCAM gene, VIM gene, SOX2 gene, OCT4 gene, c-Myc gene, Fibronectin-1 gene, Cyclin D1 gene, Matrix metallopeptidase 2 gene, CD44 gene, insulin receptor substrate 1 gene when the expression level of the OAZ1 gene is 1, respectively. The expression levels of the respective genes can be determined by methods known to those skilled in the art. For example, the expression level of each gene can be determined by collecting the total RNA of differentiation-induced endodermal cells, performing cDNA synthesis, and performing quantitative RT-PCR (qPCR) using the cDNA as a template. The expression levels of the Nanog gene, HNF1B gene, HNF4A gene, EpCAM gene, VIM gene, SOX2 gene, OCT4 gene, c-Myc gene, Fibronectin-1 gene, Cyclin D1 gene, Matrix metallopeptidase 2 gene, CD44 gene, insulin receptor substrate 1 gene are normalized by the expression level of the OAZ1 gene.

The proportion of SOX17-positive cells can be measured by, but not particularly limited to, flow cytometry. If flow cytometry using a fluorescently labeled antibody detects cells with higher fluorescence compared to the negative control (isotype control), the cells are determined as "positive" for the marker. As the fluorescently labeled antibody, any antibody known in the art can be used. Examples include, but not limited to, antibodies labeled with fluorescein isothiocyanate (FITC), phycoerythrin (PE), allophycocyanin (APC), and the like.

[9] Differentiation Induction to Pancreatic β Cells

In general, differentiation induction from endodermal cells to pancreatic β cells is generally performed in the order of endodermal cells (definitive endoderm: DE), primitive intestinal cells (Primitive Gut Tube: PGT), posterior foregut cells (Posterior Foregut: PFG), pancreatic progenitor cells (PP), endocrine progenitor cells (EP), and pancreatic β cells (pancreatic β cells: (3).

The culture temperature for inducing differentiation into pancreatic β cells is not particularly limited as long as it is a culture temperature suitable for culture of pluripotent stem cells to be used. In general, however, the temperature is 30° C. to 40° C. and preferably about 37° C.

The culture is preferably performed under a $CO_2$ concentration atmosphere of about 1 to 10%, preferably 5%, using a $CO_2$ incubator or the like.

A medium used for inducing differentiation of an endodermal cell (definitive endoderm) to a primitive gut cell (dermal endoderm) may be a medium prepared by adding B27 supplement, FGF-2 and FGF-7, EC23, SB431542, dorsomorphin, and SANT1 to a basal medium (for example, a DMEM medium).

The culture period for differentiation induction from an endothelial cell (definitive endoderm) to a primitive gut cell is generally about 24 hours to 72 hours, preferably about 36 hours to 60 hours.

A medium used for inducing differentiation of a primitive gut cell to a posterior or anterior gut cell may be a medium prepared by adding B27 supplement, FGF-2, EC23, SB431542, dorsomorphin, and SANT1 to a basal medium (for example, a DMEM medium).

The culture period for differentiation induction from a primitive gut cell to a posterior or anterior gut cell is generally about 48 hours to 144 hours, preferably about 72 hours to 120 hours.

A medium used for inducing differentiation of a posterior or anterior gut cell to a pancreatic progenitor cell may be a medium prepared by adding B27 supplement, FGF-10, EC23, dorsomorphin, ALK inhibitor II, Indolactam V, and Excendin-4 to a basal medium (for example, a DMEM medium).

The culture period for differentiation induction from a posterior or anterior gut cell to a pancreatic progenitor cell is generally about 24 hours to 120 hours, preferably about 48 hours to 96 hours.

A medium used for inducing differentiation of a pancreatic progenitor cell to an endocrine progenitor cell may be a medium prepared by adding B27 supplement, EC23, dorsomorphin, ALK inhibitor II, SANT1, and Excendin-4 to a basal medium (for example, an Advanced-DMEM medium).

The culture period for differentiation induction from a pancreatic progenitor cell to an endocrine progenitor cell is generally about 24 hours to 120 hours, preferably about 48 hours to 96 hours.

A medium used for inducing differentiation of an endocrine progenitor cell to a pancreatic β cell may be a medium prepared by adding B27 supplement, FGF-2, BMP-4, HGF, IGF-1, ALK inhibitor II, Excendin-4, nicotinamide, and Forskolin to a basal medium (for example, an Advanced-DMEM medium).

The culture period for differentiation induction from an endocrine progenitor cell to a pancreatic β cell is generally about 96 hours to 240 hours.

The pancreatic β cell obtained by the above method has a high ability to secrete insulin and can exert a high therapeutic effect on diabetes.

[10] Differentiation Induction to Mesodermal Cells or Ectodermal Cells

In the present invention, for inducing differentiation from pluripotent stem cells into mesodermal cells, for example, a method described in National Publication of International Patent Application No. 2013-530680 can be used. The publication No. 2013-530680 describes a method for producing an intermediate mesoderm cell from a human pluripotent stem cell, comprising (i) a step of culturing the human pluripotent stem cell in a medium containing Activin A and Wnt; and (ii) a step of culturing the cells obtained in the step (i) in a medium containing BMP and Wnt or a functional equivalent of Wnt. Furthermore, Albert Q Lam et al., J Am Soc Nephrol 25:1211-12225, 2015 describes that the human pluripotent stem cells can be efficiently induced to differentiate into mesodermal cells by treating it with the GSK3β inhibitor CHIR99021 and then treating it with FGF2 and retinoic acid. Likewise, in the present invention, pluripotent stem cells can be induced to differentiate into mesodermal cells using the differentiation inducer described in the above document.

For inducing pluripotent stem cells to differentiate into ectodermal cells, the present invention may employ, for example, a method for culturing pluripotent stem cells in a medium containing a BMP inhibitor (Noggin et al.) and a TGFβ/ACTIVIN inhibitor (Chambers S M. et al., Nat Biotechnol. 27, 275-280 (2009)) and a method for culturing pluripotent stem cells in a medium containing a BMP inhibitor (Noggin et al.) and a Nodal/ACTIVIN inhibitor (Beata Surnacz et al., Stem Cells, 2012; 30: 1875-1884).

The present invention will be specifically described by the following examples. However, the present invention is not limited thereto.

EXAMPLES

Example 1

<Maintenance Culture of Pluripotent Stem Cell>
(TKDN4-M Cell Line)

Human iPS cell line, TKDN4-M (THE INSTITUTE OF MEDICAL SCIENCE, THE UNIVERSITY OF TOKYO) was subjected to undifferentiation maintenance culture using a human iPS cell medium (DMEM/HAM'S F12 (FUJIFILM WAKO Pure Chemical Corporation) containing 20% KNOCKOUT SERUM REPLACEMENT (KSR; GIBCO), 1×NON-ESSENTIAL AMINO ACIDS (NEAA; FUJIFILM WAKO Pure Chemical Corporation), 55 μmoL/L 2-MERCAPTOETHANOL (2-ME; GIBCO), 7.5 NG/ML RECOMBINANT HUMAN FIBROBLAST GROWTH FACTOR (FGF2; PeproTech, Inc.), and 0.5×PENICILLIN AND STREPTOMYCIN (PS; FUJIFILM WAKO Pure Chemical Corporation)) on SNL FEEDER cells treated with MITOMYCIN-C (FUJIFILM WAKO Pure Chemical Corporation). Alternatively, the cell line was subjected to undifferentiation maintenance culture on a plate coated with VITRONECTIN (GIBCO) using an ESSENTIAL 8™ medium (E8; GIBCO) containing 1×PENICILLIN AND STREPTOMYCIN AND AMPHOTERICIN B (FUJIFILM WAKO Pure Chemical Corporation). Note that the culture was carried out by adding Y27632 in such a way that a final concentration was 10 μM only at the time of seeding. (454E2 cell line)

Human iPS cell line, 454E2 (CiRA) was subjected to undifferentiation maintenance culture using a human iPS cell medium (DMEM/HAM'S F12 (FUJIFILM WAKO Pure Chemical Corporation) containing 20% KNOCKOUT SERUM REPLACEMENT (KSR; GIBCO), 1×NON-ESSENTIAL AMINO ACIDS (NEAA; FUJIFILM WAKO Pure Chemical Corporation), 55 μmoL/L 2-MERCAPTOETHANOL (2-ME; GIBCO), 7.5 NG/ML RECOMBINANT HUMAN FIBROBLAST GROWTH FACTOR (FGF2; PeproTech, Inc.), and 0.5×PENICILLIN AND STREPTOMYCIN (PS; FUJIFILM WAKO Pure Chemical Corporation)) on SNL FEEDER cells treated with MITOMYCIN-C (FUJIFILM WAKO Pure Chemical Corporation). Alternatively, the cell line was subjected to undifferentiation maintenance culture on a plate coated with VITRONECTIN (GIBCO) using an ESSENTIAL 8™ medium (E8; GIBCO) containing 1×PENICILLIN AND STREPTOMYCIN AND AMPHOTERICIN B (FUJIFILM WAKO Pure Chemical Corporation). Note that the culture was carried out by adding Y27632 in such a way that a final concentration was 10 μM only at the time of seeding.

<Production of Clump>
(TkDN4-M Cell Line)

Human iPS cell line, TkDN4-M (THE INSTITUTE OF MEDICAL SCIENCE, THE UNIVERSITY OF TOKYO), was rinsed 3 times with the medium to detach from the SNL feeder cells treated with Mitomycin-C (FUJIFILM WAKO Pure Chemical Corporation), subsequently further rinsed once with PBS, and incubated using Accumax™ (Innova Cell Technologies, Inc.) at 37° C. for 15 minutes, followed by obtaining single cells by pipetting. TkDN4-M in the form of a single cell of $3 \times 10^7$ cells was suspended in 30 mL of an mTeSR1 medium containing 10 μM of Y27632, moved to a 30 mL single-use bioreactor (ABLE Corporation), and set on a 6-channel magnetic stirrer (ABLE Corporation) to carry out suspension culture for 1 day.
(454E2 Cell Line)
Human iPS cell line, 454E2 (CiRA), was rinsed twice with PBS, incubated using Accutase (Innova Cell Technologies, Inc.) at 37° C. for about 5 minutes, and prepared as a single cell collected by pipetting, followed by rinsing with DMEM/Ham's F12. 454E2 in the form of a single cell of $3 \times 10^7$ cells was suspended in 30 mL of a mTeSR1 containing 10 µM of Y27632, moved to a 30 mL single-use bioreactor (ABLE Corporation), and set on a 6-channel magnetic stirrer (ABLE Corporation) to carry out suspension culture for 1 day.
<Preculture of Pluripotent Stem Cell>
The cell population forming an aggregate obtained by the maintenance culture was suspended in DMEM/Ham's F12 (FUJIFILM WAKO Pure Chemical Corporation) containing 20% (volume/volume) Knockout serum replacement (KSR; Gibco), 1×non-essential amino acids (NEAA; FUJIFILM WAKO Pure Chemical Corporation), 55 µmol/L 2-mercaptoethanol (Gibco), 7.5 ng/mL recombinant human fibroblast growth factor (FGF2; PeproTech, Inc.), and 0.5×Penicillin and Streptomycin (PS; FUJIFILM WAKO Pure Chemical Corporation), moved to a 30 mL single-use bioreactor (ABLE Corporation), and set on a 6-channel magnetic stirrer (ABLE Corporation) to carry out suspension culture for 1 day.
<Differentiation Induction into Endodermal Cells (Definitive Endoderm)>
The cell population forming an aggregate obtained by the preculture was subjected to suspension culture for the first 2 days in RPMI1640 (FUJIFILM WAKO Pure Chemical Corporation) containing 0.5% Bovine Serum Albumin (BSA; Sigma-Aldrich), 0.4×PS, 1 mmol/L sodium pyruvate (FUJIFILM WAKO Pure Chemical Corporation), 1×NEAA, 80 ng/mL recombinant human activin A (PeproTech, Inc.), 50 ng/mL FGF2, 20 ng/mL recombinant bone morphogenetic protein 4 (BMP4; PeproTech, Inc.), and 3 µmol/L CHIR99021 (FUJIFILM WAKO Pure Chemical Corporation). On day 3, the suspension culture was carried out by removing BMP4, FGF2, and CHIR99021 from this medium, and, on day 4, the suspension culture was further carried out for 1 day using a medium to which 1% KSR was added. Note that the suspension culture was carried out by setting the bioreactor on a 6-channel magnetic stirrer (ABLE Corporation) to prepare a sample.

Reference Example 1

<Maintenance Culture of Pluripotent Stem Cell>
The culture was carried out in the same manner as in Example 1.
<Preculture of Pluripotent Stem Cell>
The cell populations obtained by the maintenance culture were cultured, on the SNL feeder cells treated with Mitomycin-C for the TkDN4-M cell line, or on a dish coated with Vitronectin the 454E2 cell line, for 1 day using DMEM/Ham's F12 containing 20% Knockout serum replacement, 1× non-essential amino acids, 55 µmol/L 2-mercaptoethanol, 7.5 ng/mL recombinant human fibroblast growth factor, and 0.5×Penicillin and Streptomycin while adhered onto the feeder cells or the dish.
<Differentiation Induction into Endodermal Cells (Definitive Endoderm)>
The cell population obtained by the preculture was cultured for the first 2 days using RPMI1640 containing 0.5% Bovine Serum Albumin, 0.4×PS, 1 mmol/L sodium pyruvate, 1×NEAA, 80 ng/mL recombinant human activin A, 50 ng/mL FGF2, 20 ng/mL recombinant bone morphogenetic protein 4, 3 µmol/L CHIR99021 while adhered onto a dish. On day 3, the culture was carried out by removing CHIR99021 from this medium while adhered onto the dish, and, on day 4, the culture was further carried out for 1 day using a medium to which 1% (volume/volume) KSR was added while adhered onto the dish.
[Analysis of Differentiation Efficiency]
The endodermal cell populations produced in Example 1 and Reference Example 1 were analyzed by quantitative RT-PCR and flow cytometry analysis by the following procedures to investigate differentiation efficiencies into definitive endoderm (DE).
<Quantitative RT-PCR>
The total RNA of the endodermal cells induced to differentiate was isolated and purified using ISOGEN (FUJIFILM WAKO Pure Chemical Corporation), and cDNA was synthesized using PrimeScript II (Takara Bio Inc.). Using the synthesized cDNA as a template, qPCR was carried out using GoTaq qPCR master mix (Promega Corporation) by MyiQ qPCR machine (Bio-Rad Laboratories, Inc.). The detection was carried out by the intercalation method using SYBR Green, and the gene expression level comparison was carried out by the relative quantification method by creating calibration curves. An expression level of each gene was standardized by OAZ1, which is a housekeeping gene. Note that the genes OCT4, SOX2, c-Myc, Nanog, HNH1B, and HNF4A were analyzed for samples 1 and 2. Fibronectin-1 (FN1), CyclinD1, CD44, matrix metallopeptidase 2 (MMP2), and insulin receptor substrate 1 (IRS1) were analyzed at n=3, and mean values and standard deviations were calculated from the obtained analytical values. Details thereof are described in [Table 1].
The nucleotide sequences of primers used for qPCR are as follows.

```
C-MYC F:
                                    (SEQ ID NO. 1)
GTC TCC ACA CAT CAG CAC AAC TAC

C-MYC R:
                                    (SEQ ID NO. 2)
TTC GGT TGT TGC TGA TCT GTC

HNF1B F:
                                    (SEQ ID NO. 3)
GAG ATC CTC CGA CAA TTC AAC C

HNF1B R:
                                    (SEQ ID NO. 4)
AAA CAG CAG CTG ATC CTG ACT G

HNF4A F:
                                    (SEQ ID NO. 5)
AAG AGA TCC ATG GTG TTC AAG GAC

HNF4A R:
                                    (SEQ ID NO. 6)
AGG TAG GCA TAC TCATTG TCA TCG

NANOG F:
                                    (SEQ ID NO. 7)
CGA AGA ATA GCA ATG GTG TGA C

NANOG R:
                                    (SEQ ID NO. 8)
GTT GCT CCA GGT TGA ATT GTT C

OAZ1 F:
                                    (SEQ ID NO. 9)
GTC AGA GGG ATC ACA ATC TTT CAG
```

-continued

OAZ1 R:
(SEQ ID NO. 10)
GTC TTG TCG TTG GAC GTT AGT TC

OCT4 F:
(SEQ ID NO. 11)
CGC TTC AAG AAC ATG TGT AAG CTG C

OCT4 R:
(SEQ ID NO. 12)
CTC TCA CTC GGT TCT CGA TAC TG

SOX2 F:
(SEQ ID NO. 13)
ATA AGT ACT GGC GAA CCA TCT CTG

SOX2 R:
(SEQ ID NO. 14)
AAT TAC CAA CGG TGT CAA CCT G

EPCAM F:
(SEQ ID NO. 15)
ATG ATC CTG ACT GCG ATG AGA G

EPCAM R:
(SEQ ID NO. 16)
CAG TGT CCT TGT CTG TTC TTC TGA C

VIM F:
(SEQ ID NO. 17)
GTC ACC TTC GTG AAT ACC AAG AC

VIM R:
(SEQ ID NO. 18)
AGG CAG AGA AAT CCT GCT CTC

Fibronectin-1 (FN1) F:
(SEQ ID NO. 27)
CTC TGT CAA CGA AGG CTT GAA C

Fibronectin-1 (FN1) R:
(SEQ ID NO. 28)
CAC TTC CAA AGC CTA AGC ACT G

CD44 F:
(SEQ ID NO. 29)
ATA GAA GGG CAC GTG GTG ATT C

CD44 R:
(SEQ ID NO. 30)
ATG TGT CAT ACT GGG AGG TGT TG

Cyclin D1 F:
(SEQ ID NO. 31)
CCG CAC GAT TTC ATT GAA C

Cyclin D1 R:
(SEQ ID NO. 32)
ACT TCA CAT CTG TGG CAC AGA G matrix metallopeptidase 2 (MMP2)
(SEQ ID NO. 33)
F: CAC CCA TTT ACA CCT ACA CCA AG matrix metallopeptidase 2 (MMP2)
(SEQ ID NO. 34)
R: TTG CAG ATC TCA GGA GTG ACA G insulin receptor substrate 1 (IRS1)
(SEQ ID NO. 35)
F: GTT TCA TCT CCT CGG ATG AGT ATG insulin receptor substrate 1 (IRS1)
(SEQ ID NO. 36)
R: TAG TTG CTT AGC TCC TCC TCA CC <Results of Measurement>

The results of measured gene expression levels are shown in FIG. 1 to FIG. 3 and FIG. 10 to FIG. 14.

The results of FIG. 10 to FIG. 14 are collectively shown in the following table.

TABLE 1

| | | Mean | Standard deviation |
|---|---|---|---|
| FN1 | | | |
| TKDN4-M cell line | Reference Example 1 | 0.631317 | 0.350945 |
| | Example 1 | 2.345743 | 0.927054 |
| 454E2 cell line | Reference Example 1 | 0.301568 | 0.282264 |
| | Example 1 | 1.650792 | 0.559989 |
| Cyclin D1 | | | |
| TKDN4-M cell line | Reference Example 1 | 0.02852 | 0.002075 |
| | Example 1 | 0.009411 | 0.003425 |
| 454E2 cell line | Reference Example 1 | 0.028473 | 0.00573 |
| | Example 1 | 0.010213 | 0.003221 |
| CD44 | | | |
| TKDN4-M cell line | Reference Example 1 | 0.050771 | 0.015869 |
| | Example 1 | 0.002697 | 0.00079 |
| 454E2 cell line | Reference Example 1 | 0.095363 | 0.015969 |
| | Example 1 | 0.008796 | 0.004004 |
| MMP2 | | | |
| TKDN4-M cell line | Reference Example 1 | 0.07756 | 0.004175 |
| | Example 1 | 0.011237 | 0.001718 |
| 454E2 cell line | Reference Example 1 | 0.128873 | 0.025305 |
| | Example 1 | 0.017582 | 0.001715 |
| IRS1 | | | |
| TKDN4-M cell line | Reference Example 1 | 0.002116 | 0.000543 |
| | Example 1 | 0.000659 | 0.000292 |
| 454E2 cell line | Reference Example 1 | 0.001594 | 9.76E-05 |
| | Example 1 | 0.000638 | 0.00013 |

The endodermal cells induced to differentiate by the method described in Example 1 had reduced gene expression levels of undifferentiation markers (OCT4, SOX2, c-Myc, and Nanog) compared to the endodermal cells induced to differentiate by the method described in Reference Example 1 (FIG. 1).

The endodermal cells induced to differentiate by the method described in Example 1 had increased gene expression levels of primitive gut tube markers (HNF1B and HNF4A) compared to the endodermal cells induced to differentiate by the method described in Reference Example 1 (FIG. 1).

The endodermal cells induced to differentiate by the method described in Example 1 had increased gene expression levels of Fibronectin-1 (FN1) compared to the endodermal cells induced to differentiate by the method described in Reference Example 1 (FIG. 10).

The endodermal cells induced to differentiate by the method described in Example 1 had reduced gene expression levels of Cyclin D1, CD44, matrix metallopeptidase 2 (MMP2), and insulin receptor substrate 1 (IRS1) compared to the endodermal cells induced to differentiate by the method described in Reference Example 1 (FIG. 11 to FIG. 14).

<Flow Cytometry Analysis>

The cells collected and dispersed to single cells were fixed using 4% PFA (paraformaldehyde) at room temperature for 20 minutes, subsequently washed 3 times with PBS, and permeabilized overnight at −20° C. using cold methanol. After washing 3 times with 3% FBS (fetal bovine serum)/PBS, the cells were blocked with 3% FBS (fetal bovine serum)/PBS, and stained with fluorescently labeled antibodies shown in the following table at 4° C. for 30 minutes to 1 hour. After washing once with 3% FBS (fetal bovine serum)/PBS, the cells passed through a cell strainer were analyzed using FACSVerse (Becton, Dickinson and Company; BD Biosciences).

TABLE 2

| Antibody name | Manufacturer | Catalog No. |
| --- | --- | --- |
| Anti-SOX2 antibody | BioLegend, Inc. | 656110 |
| Anti-SOX17 antibody | BD Biosciences | 562594 |
| Anti-FOXA2 antibody | BD Biosciences | 561589 |

The endodermal cells induced to differentiate by the method described in Example 1 had increased gene expression levels of EpCAM, which is an endodermal marker, compared to the endodermal cells induced to differentiate by the method described in Reference Example 1, and SOX17-positive cells accounted for 90% or more (FIG. 2 and FIG. 3).

The endodermal cells induced to differentiate by the method described in Example 1 had reduced gene expression levels of VIM, which is a mesenchymal marker, compared to the endodermal cells induced to differentiate by the method described in Reference Example 1 (FIG. 3).

Example 2

<Differentiation Induction into Pancreatic β Cell>

Differentiation induction into pancreatic β cells from the endodermal cells obtained by the methods described in Example 1 and Reference Example 1 was carried out in accordance with the method described in Yabe S G, Fukuda S, Takeda F, Nashiro K, Shimoda M, Okochi H. Efficient generation of functional pancreatic n-cells from human induced pluripotent stem cells. J Diabetes. 2017 February; 9(2):168-179. Specifically, the primitive gut tube (PGT) differentiation was carried out by culturing for 2 days using RPMI1640 containing 0.5% BSA, 1 mmol/L sodium pyruvate, 1×NEAA, 0.4×PS, 50 ng/mL FGF2, 50 ng/mL recombinant human FGF7 (PeproTech, Inc.), 2% B27 supplement (Gibco), 0.67 μmol/L EC23 (Santa Cruz Biotechnology, Inc.), 1 μmon dorsomorphin (FUJIFILM WAKO Pure Chemical Corporation), 10 μmon SB431542 (FUJIFILM WAKO Pure Chemical Corporation), and 0.25 mol/L SANT1 (FUJIFILM WAKO Pure Chemical Corporation).

The posterior foregut (PFG) differentiation was carried out by culturing for 4 days using DMEM-high glucose (FUJIFILM WAKO Pure Chemical Corporation) containing 0.4×PS, 1×NEAA, 50 ng/mL FGF2, 2% B27, 0.67 μmon EC23, 1 μmon dorsomorphin, 10 μmon SB431542, and 0.25 μmon SANT1.

The pancreatic progenitor (PP) differentiation was carried out by culturing for 3 days using DMEM-high glucose containing 0.4×PS, 1×NEAA, 50 ng/mL recombinant human FGF10 (PeproTech, Inc.), 2% B27, 0.5 μmon EC23, 1 μmol/L dorsomorphin, 0.25 μmon SANT1, 5 μmon Alk5 inhibitor II (BioVision Inc.), and 0.3 μmol/L indolactam V (ILV; Cayman Chemical).

The endocrine progenitor differentiation was carried out by culturing for 3 days using Advanced-DMEM (Gibco) containing 0.4×PS, 2 mmol/L L-glutamine, 2% B27, 0.2 μmol/L EC23, 1 μmon dorsomorphin, 0.25 μmon SANT1, 5 μmon Alk5 inhibitor II, and 50 ng/mL Exendin4 (Sigma-Aldrich).

The pancreatic β cell differentiation was carried out by culturing for 6 days using Advanced-DMEM containing 0.4×PS, 2 mmol/L L-glutamine, 2% B27, 10 ng/mL BMP4, 10 ng/mL FGF2, 50 ng/mL recombinant human hepatocyte growth factor (HGF; PeproTech, Inc.), 50 ng/mL insulin-like growth factor 1 (IGF1; PeproTech, Inc.), 5 μmon Alk5 inhibitor II, 50 ng/mL Exendin4, 5 mmol/L nicotinamide (Sigma-Aldrich), and 5 μmol/L forskolin (FUJIFILM WAKO Pure Chemical Corporation). The thus obtained cells are called iPS-β cells.

<Transplantation Experiment on Diabetes Model Mice (Diabetes Models Non-Obese Diabetic (NOD)-Severe Combined Immunodeficiency (SCID) Mice Experiment)>

The iPS-β cells obtained by the above differentiation induction into pancreatic β cells were, after rinsing once with HBSS, suspended in HBSS containing 3.33 μg/mL of iMatrix-511 (FUJIFILM WAKO Pure Chemical Corporation), and the suspended cells were transplanted under the left renal capsule ($4 \times 10^6$ cells were administered to mouse individuals 9A-1, 9A-2, and 9B-2 and $6 \times 10^6$ cells were administered to 27B-1) of diabetes models NOD/SCID mice (CLEA Japan, Inc.) using a Hamilton syringe (Hamilton Company). The diabetes model NOD/SCID mice used were individuals whose blood glucose level elevated to 250 mg/dL or more by administering 130 mg/kg of streptozotocin (STZ; Sigma-Aldrich) from the caudal vein. The transplantation (day 0) was carried out 14 days after from the STZ administration (−14 days). Casual blood glucose levels were measured by collecting blood from the caudal vein and using Glutest Neo alpha (SANWA KAGAKU KENKYUSHO CO., LTD.). Human c-peptide measurement in mouse blood was carried out by collecting a blood sample after the transplantation from the caudal vein into a Fisherbrand heparinized hematocrit tube (Fisher Scientific), centrifuging (10 min., 4° C., 800×g) the sample to separate serum, and subsequently using a human ultrasensitive C-peptide ELISA kit (Mercodia AB). Blood samples were collected from the mouse individuals 9A-1, 9A-2, and 9B-2, to which the iPS-β cells produced from the endodermal cells obtained by the method described in Reference Example 1 were transplanted, after 12 weeks from the transplantation, and from the mouse individual 27B-1, to which the iPS-β cells produced from the endodermal cells obtained by the method described in Example 1 were transplanted, after 2, 6, 11, and 16 weeks after the transplant.

FIG. 4 shows the concentrations of human c-peptide in mouse blood which was investigated to examine the in vivo function. Concentrations of human c-peptide in mouse blood were about 10 some pM on week 12 after the transplantation of the iPS-β cells produced from the endodermal cells obtained by the method described in Reference Example 1, but the concentrations of human c-peptide in mouse blood exceeded 50 pM on week 2 after the transplantation of the iPS-β cells produced from the endodermal cells obtained by the method described in Example 1, further from thereon the amount of C-peptide kept increasing and increased up to close to 300 pM on week 16. As described above, the method of the present invention succeeded to significantly increase the amount of human c-peptide in mouse blood secreted by the pancreatic β cells derived from the human iPS cells transplanted into the mice.

FIG. 5 shows the measurement results on casual blood glucose of diabetes model mice.

Non-cell transplant mouse individuals had extremely high blood glucose levels of 400 to 600 mg/dL for 140 days after the transplant, whereas the individuals to which the iPS-β cells produced from the endodermal cells obtained by the method described in Example 1 were transplanted had blood glucose levels decreasing after the transplantation, reaching down to 250 mg/dL on day 60 after the transplantation, and exhibited a substantially normal level of 125 mg/dl on day 140 after the transplant. From the findings above, the somatic cells (pancreatic β cells) obtained by the differentiation induction by the method of the present invention are revealed to be extremely effective for treating diabetes.

Example 3

<Effects of BSA and ITS in Differentiation Induction from Pluripotent Stem Cells into Endodermal Cells>

Maintenance culture and preculture of pluripotent stem cells were carried out by the method described in Example 1, and usefulness of BSA and ITS addition in the differentiation induction from pluripotent stem cells into endodermal cells were validated by the following method. iPS cell lines used were 253G1 (CiRA) and 454E2 (CiRA).

Under the first condition, the cell lines were cultured for the first 2 days using RPMI1640 containing 10 mg/mL (1.0%) Bovine Serum Albumin, 0.4×PS, 1 mmol/L sodium pyruvate, 1×NEAA, 80 ng/mL activin A, 50 ng/mL FGF2, 20 ng/mL BMP4, 3 μmol/L CHIR99021, and 1:50000 ITS-X (Gibco). On day 3, the culture was carried out by removing BMP4, FGF2, and CHIR99021 from this medium, and the culture was further carried out for 1 day using a medium to which 1% KSR was added.

Under the second condition, the cell lines were cultured for the first 2 days using RPMI1640 containing 2.5 mg/mL (0.25%) Bovine Serum Albumin, 0.4×PS, 1 mmol/L sodium pyruvate, 1×NEAA, 80 ng/mL activin A, 50 ng/mL FGF2, 20 ng/mL BMP4, 3 μmol/L CHIR99021, and 1:5000 ITS-X. On day 3, the culture was carried out by removing BMP4, FGF2, and CHIR99021 from this medium, and the culture was further carried out for 1 day using a medium to which 1% KSR was added.

The total RNA of the endodermal cell population induced to differentiate by these methods was isolated and purified using ISOGEN (FUJIFILM WAKO Pure Chemical Corporation) to investigate a differentiation efficiency into the endodermal cells, and cDNA was synthesized using PrimeScript II (Takara Bio Inc.). Using the synthesized cDNA as a template, qPCR was carried out using GoTaq qPCR master mix (Promega Corporation) by MyiQ qPCR machine (Bio-Rad Laboratories, Inc.). The detection was carried out by the intercalation method using SYBR Green, and the gene expression level comparison was carried out by the relative quantification method by creating calibration curves. Expression levels of an undifferentiation marker OCT3/4 and a differentiation marker SOX17 were standardized by OAZ1, which is a housekeeping gene.

The nucleotide sequences of primers used for qPCR are as follows.

```
OAZ1-F:
                                      (SEQ ID NO. 19)
GTC AGA GGG ATC ACA ATC TTT CAG

OAZ1-R:
                                      (SEQ ID NO. 20)
GTC TTG TCG TTG GAC GTT AGT TC

OCT4-F:
                                      (SEQ ID NO. 21)
CGC TTC AAG AAC ATG TGT AAG CTG C

OCT4-R:
                                      (SEQ ID NO. 22)
CTC TCA CTC GGT TCT CGA TAC TG
```

```
-continued
SOX17-F:
                                      (SEQ ID NO. 23)
TAC ACA CTT CCT GGA GGA GCT AAG SOX17-R:
                                      (SEQ ID NO. 24)
CCA AAC TGT TCA AGT GGC AGA C FOXA2-F:
                                      (SEQ ID NO. 25)
GAG ATC TAC CAG TGG ATC ATG GAC FOXA2-R:
                                      (SEQ ID NO. 26)
CAC CTT CAG GAA ACA GTC GTT G
```

The above measurement results are shown in FIG. 6.

Under both conditions of 1% BSA-1:50000 ITS-X and 0.25% BSA-1:5000 ITS-X, expression levels of SOX17 and FOXA2 of DE marker were high, thereby confirming that efficient differentiation induction was carried out. Note that the samples cultured under the condition of 0.25% BSA-1:5000 ITS-X rather than the condition of 1% BSA-1:50000 ITS-X had the expression levels of undifferentiation marker, OCT4, more notably decreased, whereas the expression levels of endodermal markers, SOX17 and FOXA2, were more notably increased, thereby confirming that 0.25% BSA-1:5000 ITS-X is more effective than the condition of 1% BSA-1:50000 ITS-X.

Example 4

<Effect of 2-Mercaptoethanol in Differentiation Induction from Pluripotent Stem Cells into Endodermal Cells>

Maintenance culture and preculture of pluripotent stem cells were carried out by the method described in Example 1, and usefulness of 2-mercaptoethanol addition in the differentiation induction from pluripotent stem cells into endodermal cells were validated by the following method.

The cells cultured to a subconfluent state (about 80%) were detached and collected using Accutase (Innova Cell Technologies, Inc.), pelletized, subsequently resuspended by adding Essential 8™ containing 10 mg/mL of BSA and 10 μM of Y27632 in such a way as to contain 5×10$^5$ cells per mL, and seeded in a 6-well plate for suspension culture (Sumitomo Bakelite Co., Ltd.) in a proportion of 4 ml/well. The cells were cultured overnight on an orbital shaker (Optima Co., Ltd.) at a rotation speed of 90 rpm to produce a cell clump. Subsequently, the medium was replaced with 20% Knockout serum replacement, 1×non-essential amino acids, 55 μmol/L 2-mercaptoethanol, 7.5 ng/mL recombinant human fibroblast growth factor, and 1×Penicillin and Streptomycin and Amphotericin B to carry out the culture for 1 day, followed by carrying out definitive endoderm (DE) differentiation for 4 days. For the first 1 day, the cells were cultured by adding 55 μmol/L 2-mercaptoethanol or 1% N21 supplement (R&D Systems, Inc.) to RPMI1640 containing 0.5% Bovine Serum Albumin, 1×PSB, 1 mmol/L sodium pyruvate, 1×NEAA, 80 ng/mL activin A, 50 ng/mL FGF2, 20 ng/mL BMP4, and 3 μmol/L CHIR99021. On day 2 and day 3, the culture was carried out by removing BMP4, FGF2, and CHIR99021 from this medium, changing the concentration of activin A to 100 ng/mL, and adding 55 μmol/L 2-mercaptoethanol or 1% N21 supplement, and on day 4, the culture was further carried out for 1 day using a medium to which 1% KSR was added.

<Cell Density Counting>

After inducing to differentiate into endodermal cells, the cells were treated with Accutase at 37° C. for 5 to 10 minutes, monodispersed by pipetting, stained with trypan blue, and subsequently a cell count in the cell population induced to differentiate into endodermal cells was counted using a hemocytometer to measure a cell density.

<Flow Cytometry Analysis>

After differentiation induction into endodermal cells, the cells collected and dispersed to single cells were fixed using 4% PFA (paraformaldehyde) at room temperature for 20 minutes, subsequently washed 3 times with PBS, and permeabilized overnight at −20° C. using cold methanol. After washing 3 times with 3% FBS (fetal bovine serum)/PBS, the cells were blocked with 3% FBS (fetal bovine serum)/PBS, and stained with fluorescently labeled antibodies shown in the following table at 4° C. for 30 minutes to 1 hour. After washing once with 3% FBS (fetal bovine serum)/PBS, the cells passed through a cell strainer were analyzed using FACSVerse (Becton, Dickinson and Company; BD Biosciences).

TABLE 3

| Antibody name | Manufacturer | Catalog No. |
| --- | --- | --- |
| Anti-SOX2 antibody | BioLegend, Inc. | 656110 |
| Anti-SOX17 antibody | BD Biosciences | 562594 |

In the above, an experiment was also conducted such that culture was carried out in the same manner except that 55 μmol/L 2-mercaptoethanol was not used.

In the above, experiments were also conducted using the same method except that N21-MAX Media Supplement (R & D Systems) (but in the absence of insulin) was used instead of 55 μmol/L 2-mercaptoethanol. The composition excluding insulin from the N21-MAX Media Supplement is as follows:

albumin (bovine), L-carnitine, catalase, corticosterone, ethanolamine, glutathione, galactose, transferrin, linoleic acid, linolenic acid, lipoic acid, progesterone, putrescine, retinyl acetate, retinol, selenite, superoxide dismutase, triiodo-L-thyronine, D,L-alpha-tocophenol, and D,L-alpha-tocophenol acetate.

FIG. 7 shows the results of measurement of the proportion of cells positive for SOX2 and SOX17 by FACS on the cells after the above culture (Day 5). Furthermore, FIG. 8 shows the measurement results of the cell density of cells after the above culture (Day 5).

Differentiation into endodermal cells was observed in both the case with the addition of 2-mercaptoethanol and the case with no addition of 2-mercaptoethanol. In addition, in the case with the addition of 2-mercaptoethanol, an increase in the number of viable cells was also found from the measurement results of the cell density. Furthermore, in the case with the use of a composition excluding insulin from N21-MAX Media Supplement, an increase in the number of viable cells was also observed. Furthermore, it was found that the case with the addition of 2-mercaptoethanol causes a decrease in undifferentiated residual rate (SOX2 positive cell rate). Even in the case with the addition of 2-mercaptoethanol, there was no substantial change in endodermal differentiation efficiency (SOX17 positive cell ratio and FOXA2 positive cell ratio).

Example 5

<Experimental Study on FGF2 and TGFβ1 in Preculture of Pluripotent Stem Cell>

After subjecting the TkDN4-M strain to the undifferentiated maintenance described in Example 1, the cells cultured to subconfluent (about 80%) were detached by Accutase, collected and pelleted. Then, Essentil 8 containing 10 mg/mL of BSA and 10 μM of Y27632 was added at 4 mL into each well. Subsequently, the pelleted cells were suspended in the wells and cultured on an orbital shaker at 90 rpm for 12 hours to prepare cell aggregates.

In pre-culturing the prepared cell aggregate, the cells were cultured for one day in an Essential 6 medium (FGF 2 free and TGF-β1 free) containing 5 mg/mL BSA, 1×NEAA, 55 μmol/L 2-mercaptoethanol, and 1×PS. Subsequently, Sample 1 in which differentiation induction described in Example 1 was started was prepared. Furthermore, in pre-culturing the prepared cell aggregate separately, the cells were cultured for one day in an Essential 8™ medium containing 5 mg/mL BSA, 1×NEAA, 55 μmol/L 2-mercaptoethanol, 1×PS. Subsequently, Sample 2 starting differentiation induction as described in Example 1 was prepared. The differentiation induction efficiencies of Samples 1 and 2 thus prepared were verified by a flow cytometry analysis shown below.

<Flow Cytometry Analysis>

After the induction of differentiation into endodermal cells, the cells were collected and dispersed to individual single cells. Then the cells were fixed with 4% PFA (paraformaldehyde) for 20 minutes at room temperature, followed by being washed three times with PBS and permeabilized with cold methanol overnight at −20° C. After washing 3 times with 3% FBS (fetal bovine serum)/PBS, the cells were blocked with 3% FBS (fetal bovine serum)/PBS, and stained with fluorescently labeled antibodies shown in the following table at 4° C. for 30 minutes to 1 hour. After washing once with 3% FBS (fetal bovine serum)/PBS, the cells passed through a cell strainer were analyzed using FACSVerse (Becton, Dickinson and Company; BD Biosciences).

TABLE 4

| Antibody name | Manufacturer | Catalog No. |
| --- | --- | --- |
| Anti-SOX2 antibody | Biolegend | 656110 |
| Anti-SOX17 antibody | BD Biosciences | 562594 |
| Anti-FOXA2 antibody | BD Biosciences | 561589 |

FIG. 9 shows the results of measurement of the proportion of cells positive for SOX17 and FOXA2 by FACS on the cells after the above culture (Day 4).

In each of Samples 1 and 2, differentiation induction to endodermal cells was observed. Furthermore, it was revealed that the efficiency of differentiation induction to endodermal cells was higher in Sample 1 than in Sample 2. In other words, it was revealed that, in the preculture of pluripotent stem cells, the use of a medium with no addition of FGF2 and TGFβ1 improves the efficiency of differentiation induction to endodermal cells.

Example 6

<Effect of Glucose on Differentiation Induction of Pluripotent Stem Cells to Endodermal Cells>

(Preparation of Clump)

The TkDN-4 strain maintained and cultured by the method of Example 1 was rinsed once with PBS, peeled off by treatment with Accutase for 3 to 5 minutes, and dispersed into single cells. The cells were suspended in an Essential 8™ medium containing BSA (Wako Pure Chemical Industries, Ltd.) and 10 μM Y-27632 (Wako Pure Chemical Industries, Ltd.) at a final concentration of 5 mg/mL. A portion of the cells was stained with trypan blue and the number of the cells was counted. The number of the cells contained in the culture was adjusted to 5×10$^5$ cells per mL. The cells were seeded at a density of 4 mL/well into a suspension culture 6-well plate (Sumitomo Bakelite Co., Ltd.). The plate seeded with the cells was incubated in gyratory culture on a rotary shaker (Optima Co., Ltd.) at a speed of 90 rpm so as to draw a circle with a gyratory width (diameter) of 25 mm along the horizontal plane to carry out suspension culture for one day under environmental conditions of 5% $CO_2$ at 37° C.

(Preculture)

The cell population forming the aggregates obtained by the above maintenance culture was resuspended in DMEM/Ham's F12 (Wako) containing a 20% (v/v) Knockout serum replacement (KSR; Gibco), 1× non-essential amino acids (NEAA; Wako), 55 μmol/L 2-mercaptoethanol (2-mercaptoethanol; Gibco), 7.5 ng/mL recombinant human fibroblast growth factor (FGF2; Peprotech), and 0.5×Penicillin and Streptomycin (PS; Wako). Then, the cells were seeded at a density of 4 mL/well into a suspension culture 6-well plate (Sumitomo Bakelite Co., Ltd.). The plate seeded with the cells was incubated in gyratory culture on a rotary shaker (Optima Co., Ltd.) at a speed of 90 rpm so as to draw a circle with a gyratory width (diameter) of 25 mm along the horizontal plane to carry out suspension culture for one day under environmental conditions of 5% $CO_2$ at 37° C.

(Differentiation Induction to Endodermal Cells (Definitive Endoderm))

The cell population forming the aggregates obtained by the above maintenance culture was suspended and cultured on the first day in a medium prepared by addition of glucose to glucose-free RPMI1640 (Wako) containing 0.5% Bovine Serum Albumin (BSA; Sigma), 0.4×PS, 1 mmol/L sodium pyruvate (Wako), 1×NEAA, 80 ng/mL recombinant human activin A (Peprotech), 50 ng/mL FGF2, 20 ng/mL recombinant bone morphogenetic protein 4 (BMP4; Peprotech), and 3 μmol/L CHIR99021 (Wako) so as to reach to each final concentration (0 g/L, 0.5 g/L, 1 g/L, or 2 g/L, or 4 g/L).

On the second and third days, the cells were suspended and cultured in the medium after removal of BMP4, FGF2, and CHIR99021 therefrom. Incidentally, the glucose concentration in the medium on the second and third days was 0 g/L, 0.5 g/L, 1 g/L, 2 g/L, or 4 g/L as in the first day. Suspension culture was performed by seeding the cells at a density of 4 mL/well into a suspension culture 6-well plate (Sumitomo Bakelite Co., Ltd.) in gyratory culture on a rotary shaker (Optima Co., Ltd.) at a speed of 90 rpm so that it draws a circle with a gyratory width (diameter) of 25 mm along the horizontal plane under environmental conditions of 5% $CO_2$ at 37° C.

On the fourth day (Day 4), the cell density in the cell population induced to differentiate into endodermal cells by the following procedure was measured.

<Cell Density Counting>

After induction of differentiation into endodermal cells, the cells were treated with Accutase for 5 to 10 minutes at 37° C. and monodispersed by pipetting, followed by being stained with trypan blue. Then, the number of cells was counted using a hemocytometer, and the cell density of the cell population induced to differentiate into endodermal cells was measured.

The measurement results of cell density are shown in FIG. 15. It was found that the cell density increases as the glucose concentration decreases. However, a glucose concentration of 0 g/L resulted in killing of cells.

Analysis of gene expression of cell population induced to differentiate into endodermal cells was carried out by quantitative RT-PCR (the procedures were as described in Example 1 and Reference Example 1) on the first to fourth days (Day 1 to Day 4). The results are shown in FIGS. 16 to 18.

The results of FIG. 16 and FIG. 17 prove that a glucose concentration of 1.0 g/L or less tends to cause a decrease in undifferentiated cells (SOX2 positive cells and Nanog positive cells).

The results in FIG. 18 suggest that the endodermal differentiation proceeds earlier as the glucose concentration decreases.

On the fourth day, the positive rates of SOX2 and SOX17 were determined by flow cytometric analysis as follows:

<Flow Cytometry Analysis>

After differentiation induction into endodermal cells, the cells collected and dispersed to single cells were fixed using 4% PFA (paraformaldehyde) at room temperature for 20 minutes, subsequently washed 3 times with PBS, and permeabilized overnight at −20° C. using cold methanol. After washing 3 times with 3% FBS (fetal bovine serum)/PBS, the cells were blocked with 3% FBS (fetal bovine serum)/PBS, and stained with fluorescently labeled antibodies shown in the following table at 4° C. for 30 minutes to 1 hour. After washing once with 3% FBS (fetal bovine serum)/PBS, the cells passed through a cell strainer were analyzed using FACSVerse (Becton, Dickinson and Company; BD Biosciences).

TABLE 5

| Antibody name | Manufacturer | Catalog No. |
|---|---|---|
| Anti-SOX2 antibody | BioLegend, Inc. | 656110 |
| Anti-SOX17 antibody | BD Biosciences | 562594 |

The results of flow cytometry analysis are shown in FIG. 19.

The results in FIG. 19 prove that a glucose concentration of 1.0 g/L or less tends to cause a decrease in undifferentiated cells (SOX2 positive cells). Undifferentiated iPS cells (SOX2 positive cells) have high glucose requirements. Under conditions of a glucose concentration of 1.0 g/L or less, it is presumed that undifferentiated cells (SOX2 positive cells) could not survive and were killed.

Example 7

<Effect of Glucose on Differentiation Induction of Pluripotent Stem Cells to Endodermal Cells>

Differentiation induction of pluripotent stem cells to endodermal cells was performed in a manner similar to Example 6, except that the concentration (g/L) of glucose in the medium on the first, second, and third days as shown in following table.

TABLE 6

|  | Day 1 | Day 2 | Day 3 |
|---|---|---|---|
| Experiment 1 | 2 | 2 | 2 |
| Experiment 2 | 2 | 2 | 0.5 |
| Experiment 3 | 2 | 0.5 | 0.5 |
| Experiment 4 | 0.5 | 0.5 | 0.5 |

FIG. 20 shows the results of measurement of positive ratios of SOX2 and SOX17 in the cell population induced to differentiate into endodermal cells by flow cytometric analysis in a manner similar to Example 6 on the fourth day.

The results in FIG. 20 prove that the longer the culture period at a glucose concentration of 0.5 g/L the more SOX2 positive cells decrease and the more SOX17 positive cells increase.

In addition, FIG. 21 shows the results of the above flow cytometry analysis. The left panel of FIG. 21 shows the case of Experiment 1, and the right panel of FIG. 21 shows the case of Experiment 4.

The results in FIG. 21 prove that culturing the cells at a glucose addition concentration of 0.5 g/L results in a decrease in SOX2 positive cells and an increase in SOX17 positive cells.

The invention claimed is:

1. A method for producing an endodermal cell from a pluripotent stem cell, the method comprising the following (a) to (b):
   (a) a step of suspension culture of a pluripotent stem cell using a medium containing 2-mercaptoethanol to prepare a cell population, and
   (b) a step of culturing the cell population obtained by step (a) using a medium containing activin A, FGF2 and BMP4, and subsequently culturing using a medium to which FGF2 and BMP4 are not added.

2. The production method according to claim 1, wherein, to the medium containing 2-mercaptoethanol, activin A is not added.

3. The production method according to claim 1, wherein, to the medium containing 2-mercaptoethanol, a WNT signaling activator is not added.

4. The production method according to claim 1, wherein, to the medium containing 2-mercaptoethanol, FGF2 is not added.

5. The production method according to claim 1, wherein, to the medium containing 2-mercaptoethanol, TGFβ1 is not added.

6. The production method according to claim 1, wherein the medium containing 2-mercaptoethanol further contains insulin.

7. The production method according to claim 1, wherein the medium to which FGF2 and BMP4 are not added contains at least one selected from the group consisting of insulin, transferrin, sodium selenite, and ethanolamine.

8. The method according to claim 1, wherein the medium containing activin A, FGF2 and BMP4 and/or the medium to which FGF2 and BMP4 are not added further contains 2-mercaptoethanol.

9. The method according to claim 1, wherein the medium containing activin A, FGF2 and BMP4 and/or the medium to which FGF2 and BMP4 are not added contains glucose in a concentration of 1.0 g/L or less.

10. The method according to claim 1, wherein the proportion of undifferentiated cells is reduced, and a cell population is provided that includes endodermal cells capable of differentiating into somatic cells.

11. The method according to claim 1, wherein the medium containing activin A, FGF2 and BMP4 further contains WNT signaling activator.

* * * * *